United States Patent [19]

McBride et al.

[11] Patent Number: 5,080,884
[45] Date of Patent: Jan. 14, 1992

[54] HYDROCARBYLPHENYL DIAMINODITHIOL RADIONUCLIDE COMPLEXES AND THEIR USE IN IMAGING

[75] Inventors: William J. McBride, Oakland; Ronald M. Baldwin, Concord; Janice M. Kerr, San Jose; Lisa M. Schultze, Oakland; Nilda Salazar, Hercules; James M. Chinitz, Oakland, all of Calif.

[73] Assignee: Medi-Physics, Inc., Arlington Heights, Ill.

[21] Appl. No.: 660,403

[22] Filed: Feb. 22, 1991

Related U.S. Application Data

[60] Division of Ser. No. 576,163, Aug. 30, 1990, Pat. No. 5,026,913, which is a continuation of Ser. No. 445,212, Dec. 12, 1989, abandoned.

[51] Int. Cl.$^5$ .................. A61K 49/02; C07F 13/00
[52] U.S. Cl. ............................ 424/1.1; 534/10; 534/14
[58] Field of Search .................. 424/1.1; 534/14, 10

[56] References Cited

U.S. PATENT DOCUMENTS

| | | | |
|---|---|---|---|
| 4,575,556 | 3/1986 | Byrne et al. | 549/ |
| 4,615,876 | 10/1986 | Troutner et al. | 424/ |
| 4,638,051 | 1/1987 | Burns et al. | 534/ |
| 4,670,545 | 6/1987 | Fritzberg et al. | 534/ |
| 4,705,849 | 11/1987 | Nunn et al. | 534/ |
| 4,714,605 | 12/1987 | Feld et al. | 424/ |

FOREIGN PATENT DOCUMENTS

| | | |
|---|---|---|
| 179608A | 4/1986 | European Pat. Off. |
| 194843A | 9/1986 | European Pat. Off. |
| 199260A | 10/1986 | European Pat. Off. |
| 229718A | 7/1987 | European Pat. Off. |

OTHER PUBLICATIONS

J. Nucl. Med. 26:105 (1985).
J.C.S. Dalton 1798 (1981).
J. Nucl. Med. 25:326–332 (1984).
Bryson et al., Inorg. Chem., 27:2154–2161 (1988).

Primary Examiner—John S. Maples
Attorney, Agent, or Firm—Marshall, O'Toole, Gerstein, Murray & Bicknell

[57] ABSTRACT

An agent for imaging organs using a radioactive complex of a radioactive metal with a benzene ring having two 2-mercapto-2-methylpropylamino substituents where one of these mercapto substituents is substituted with a hydrocarbyl group.

49 Claims, No Drawings

HYDROCARBYLPHENYL DIAMINODITHIOL RADIONUCLIDE COMPLEXES AND THEIR USE IN IMAGING

This is a division of application Ser. No. 07/576,163, now U.S. Pat. No. 5,026,913 filed Aug. 30, 1990 which is a continuation of application Ser. No. 07/445,212 filed Dec. 12, 1989, abandoned.

SUMMARY OF THE INVENTION

In accordance with this invention, we have discovered that radionuclide complexes of a compound of the formula:

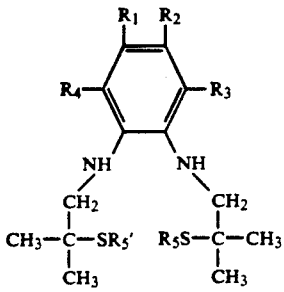

wherein $R_1$, $R_2$, $R_3$ and $R_4$ are halogen, hydrogen or lower alkyl, with at least one of $R_3$ and $R_4$ being hydrogen; and one of $R_5$ and $R_5'$ being hydrogen whereas the other of said $R_5$ and $R_5'$ being alkyl containing from 1 to 10 carbon atoms, alkenyl containing 2 to 10 carbon atoms, alkynyl containing from 2 to 10 carbon atoms or lower alkylcycloloweralkyl;

or pharmaceutically acceptable salt thereof; are useful for imaging various organs of the body such as the brain, heart, kidney and liver. The compounds of formula I and their salts demonstrate rapid accumulation in various organs and have the ability to penetrate the "blood/brain barrier".

In contrast to brian perfusion agents such as described in J. Nucl. Med. 26:P105 (1985) and Baldas, J. C.S. Dalton, 1981 1798 and Kung, J. Nucl. Med. 25:326-332, 1984 which are technetium-99m complexes of diaminodithiols having the following formula:

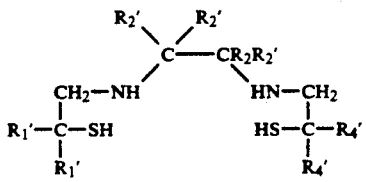

where $R_1'$, $R_2'$ and $R_4'$ are hydrogen or lower alkyl. The compounds of formula I and their pharmaceutically acceptable salts have greater uptake in various organs of the body, in particular the brain. Also the compounds of formula I and their salts have a greater ability to penetrate the blood/brain barrier and demonstrate rapid localization of the radioactivity following intravenous administration. These properties make the compounds of formula I above and their pharmaceutically acceptable salts suitable as in vivo imaging agents for diagnosing diseases and disorders of various organs such as the brain.

DETAILED DESCRIPTION

As used throughout this application, the term "lower alkyl" includes both straight chain and branched chain saturated aliphatic hydrocarbon groups containing from 1 to 7 carbon atoms said methyl, ethyl, propyl, isopropyl, butyl and isobutyl, etc. The term alkenyl designates both straight and branched chain aliphatic hydrocarbon groups containing from 2 to 10 carbon atoms and having an olefinic double bond, such as vinyl, allyl, prop-2-en-1-yl, etc. The term alkynyl designates both straight and branched chain aliphatic hydrocarbon groups containing from 2 to 10 carbon atoms and having an acetylenic triple bond, such as propargyl. The term cycloloweralkyl designates cycloaliphatic saturated hydrocarbon groups containing from 3 to 6 carbon atoms such as cyclopropyl, cyclobutyl and cyclohexyl. The term lower alkylcycloloweralkyl designates lower alkylcycloloweralkyl groups connected to the thio group on the compound of formula I via the lower alkyl substituent wherein lower alkyl and cycloloweralkyl are defined above.

As further used herein, the term "halogen" or "halo", unless otherwise stated, comprehends all halogens such as fluorine, chlorine, bromine and iodine. Alkali metal includes all alkali metal such as lithium, sodium and potassium.

As also used herein, the term "aryl" signifies both monovalent mononuclear aromatic hydrocarbon groups such as phenyl and monovalent polynuclear aryl groups such as naphthyl, anthryl, phenanthryl, etc. The preferred aryl groups are the phenyl, naphthyl and anthryl. The term arylene designates the divalent aromatic hydrocarbon groups such as phenylene, naphthalene, etc.

The term "aryl, lower alkyl" designates aryl lower alkyl substituents where aryl and lower alkyl groups are defined above, particularly benzyl.

The term "lower alkanoyl" as used throughout this specification designates "lower alkanoyl" groups containing from 2 to 7 carbon atoms such as acetyl, propionyl, etc. The term "arylloweralkanoyl" designates monovalent arylloweralkanoyl groups where aryl and lower alkanoyl are defined as above with phenylacetyl being preferred. The term "aroyl" defines aroyl groups where the aryl group is defined as above with benzoyl being preferred.

As used herein, the term "thiol protecting group" includes all of the conventional groups which are commonly employed to protect the thiol moiety. Among these groups are included lower alkylaminocarbonyl such as ethylaminocarbonyl, loweralkanoylaminomethyl, aroylaminomethyl, triarylmethyl such as triphenylmethyl, aroyl such as benzoyl, aryloxycarbonyl such as phenoxycarbonyl, arylloweralkoxylcarbonyl, preferably arylmethoxycarbonyl such as benzyloxycarbonyl, lower alkoxycarbonyl such as t-butoxycarbonyl. Among the preferred lower alkanoylaminomethyl groups is acetamidomethyl and among the preferred aroylaminomethyl is benzoylaminomethyl. The thiol protecting groups are removable by treatment with heavy metallic ions such as mercuric ions, technetium ions, silver ions, as well as any of the radioactive metals which form the complex. Any of the conventional methods commonly employed in removing these thiol protecting groups can be utilized in accordance with this invention.

In accordance with one preferred embodiment, $R_1$, $R_2$ and $R_3$ are hydrogen. When one of $R_5$ and $R_5'$ are alkyl, the preferred alkyl group has the formula:

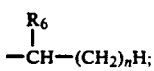

wherein n is an integer of from 0 to 5, and $R_6$ is H or —$CH_3$.

When one of $R_5$ and $R_5'$ is an alkenyl group, preferably the group has only one olefenic double bond and most preferably has the formula:

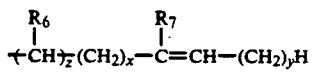

wherein $R_7$ is hydrogen or —$CH_3$; $R_6$ is as above; x is an integer from 0 to 3; z is an integer from 0 to 1 and y is an integer from 0 to 2

When one of $R_5$ and $R_5'$ is an alkynyl group, the group preferably has only one acetylenic triple bond and most preferably has the formula:

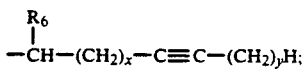

where $R_6$, x and y are as above.

When one of $R_5$ and $R_5'$ is cycloalkylloweralkyl, preferably the group has the formula:

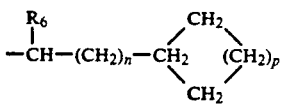

wherein n and $R_6$ are as above and p is an integer from 0 to 3.

The radionuclide for use in this invention can be any radioactive metal capable of pharmaceutical administration. Among the radioactive metals are included radioactive isotopes of indium, technetium, ruthenium or gallium. Among the radioactive isotopes are included indium-111, indium-113m, indium-114m, technetium-99m, ruthenium-97 and gallium-67, with technetium-99m being especially preferred.

The compound of formula I as well as the complex formed from the compound of formula I may form acid addition salts due to the presence of the amine functional groups. Any conventional acid addition salt capable of intravenous administration can be utilized in accordance with this invention. Among the suitable acids which can be utilized to form the salts of the complex formed from the compound of formula I include inorganic acids such as hydrochloric acid, hydrobromic acid, sulfuric acid, and the like.

In accordance with one embodiment of this invention, the compound of formula I is formed by reacting a compound of the formula

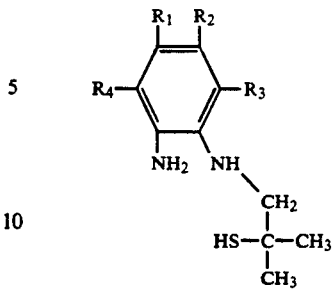

with a compound of the formula:

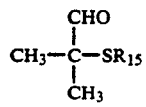

wherein $R_1$, $R_2$, $R_3$, $R_4$ are as above; and $R_{15}$ is alkyl containing from 1 to 10 carbon atoms, alkenyl containing, from 2 to 10 carbon atoms or alkynyl containing from 2 to 10 carbon atoms, or lower alkylcycloloweralkyl.

In the condensation of the compound of the formula III with a compound of formula IV to produce the compound of formula I, any conventional method of condensing an aldehyde with a primary amine can be utilized. Among the preferred methods for carrying out this condensation is by condensing the aldehyde with the amine in the presence of an organic acid such as a lower alkanoic acid to produce a Shiff Base, and thereafter reducing the Shiff Base with a hydride reducing agent. Any conventional hydride reducing agent can be utilized to carry out this reaction, with the preferred reducing agents being lithium aluminium hydride and sodium cyanoborohydride. This reaction can be carried out in an inert organic solvent. Furthermore, this reaction can be carried out without the presence of the organic acid. However, for best results it is preferable that acid be present. Furthermore, the reaction can be carried out by simply mixing the compound of formula III with the compound of formula IV in an inert organic solvent medium containing the hydride reducing agent. In carrying out this reaction any conventional inert organic solvent can be utilized. Furthermore, temperatures and pressures are not critical and this reaction can be carried out at room temperature and atmospheric pressure. On the other hand, if desired, elevated or reduced temperatures can be utilized.

The compound of formula III can be prepared by reacting o-phenylenediamine with isobutylene sulfide in accordance with the procedure disclosed in Synder, et al., J. Am. Chem. Soc. 69:2672–274 (1974). This reaction can be carried out by heating o-phenylenediamine and isobutylene sulfide in a closed system such as a bomb to temperatures greater than the boiling point of isobutylene sulfide. In accordance with this process, the corresponding compound of formula III where both amino groups are substituted with a 2-mercapto-2-methyl propyl substituent (XI) is formed in a small amount. This disubstituted compound can be removed from the compound of formula III by conventional means such as extraction or crystalization.

The compound of formula IV can be prepared from the dialdehyde of the formula:

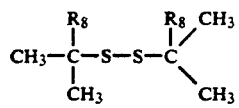   V when R$_8$ is a protected carbonyl group.

In compound formula V, R$_8$ can be any protected carbonyl group such as an acetal protected carbonyl. The term protected carbonyl group refers to a group which may be hydrolyzed to regenerate a carbonyl group under conventional hydrolysis conditions. These groups include those formed when the carbonyl is protected as a di(loweralkyl)-acetal, an alkylene acetal or an arylene acetal. Example of di(loweralkyl)-acetals are dimethyl acetals, diethyl acetals, etc. Alkylene acetals are derived from 1,2 or 1,3-glycols, such as ehtylene glycol, 1,3-propylene glycol, 2,3-butylene glycol, etc. Arylene acetals are derived from catechols such as phenylene-1,2-diols, alkyl-phenylene-1,2-diols, naphthalene-1,2-or-2,3-diols. The compound of formula V is derived from the corresponding compound where R$_8$ is a carbonyl group by conventional treatment to form the desired acetal.

The compound of formula V is converted to the compound of formula IV via the following intermediates

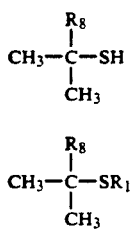   VI

VII wherein R$_8$ and R$_{15}$ are as above.

In converting the compound of formula V to the compound of formula VI, the compound of formula V is reduced in an anhydrous medium. In this respect, any conventional method of anhydrous reduction can be used to carry out this conversion. Generally, it is preferred to carry out this reduction by treating the Compound V with an alkali metal such as sodium metal in liquid ammonia. In carrying out this reaction, the temperature below the boiling point of liquid ammonia is utilized.

The compound of formula VI can be converted to the compound of formula VII by reacting the compound of formula VI with a halide of the formula:

R$_{15}$X   VIII wherein R$_{15}$ is as above; and
X is a halogen.
Among the preferred compounds of formula VIII are compounds of the formula:

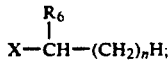   VIII-A wherein X, n and R$_6$ are as above,

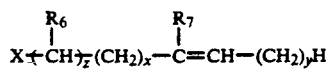   VIII-B wherein X, R$_6$, R$_7$, x, y and z are as above,

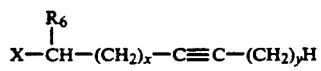   VIII-C wherein R$_6$, X, x and y are as above,

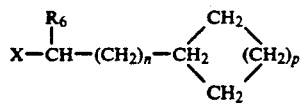   VIII-D wherein X, n, p and R$_6$ are as above.

In reacting the compound of formula VI with the halide of formula VIII, any conventional method for condensing a thiol with an organic halide can be used to form the compound of formula VII. Among the preferred methods is to condense the compound of formula VI with the compound of formula VIII in the presence of a base. Any conventional base can be utilized in this reaction. Among the preferred bases are the alkali metal hydrides, alkali metal hydroxides or alkali metal carbonates. Generally this reaction is carried out in an inert organic solvent medium. Any conventional inert organic solvent can be used as the reaction medium with ethers such as tetrahydrofuran as well as lower alkanols such as methanol being especially preferred. If a lower alkanol is used as the organic solvent, the solvent may also contain water. In carrying out this reaction of the compound of formula VII with a halide, temperature and pressure are not critical and this reaction can be carried out at room temperature and atmospheric pressure. If desired, higher or lower temperatures can be utilized.

The compound of formula VII can be converted to the compound of formula IV by acid hydrolysis in an aqueous medium. Any conventional method of hydrolyzing a ketal into the corresponding carbonyl group can be used in this conversion.

In accordance with another embodiment, the compound of formula I can be prepared from o-phenylenediamine via the following intermediates:

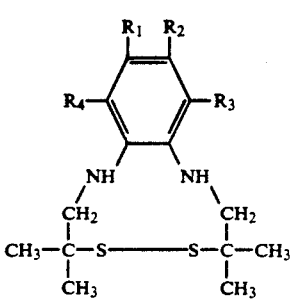   X

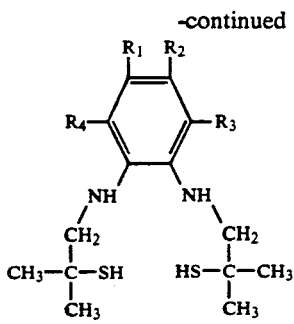

XI wherein $R_1$, $R_2$, $R_3$ and $R_4$ are as above.

The reaction of o-phenylenediamine to produce the compound of formula X is carried by reacting o-phenylene diamine with the precursor of the compound of V, i.e. the compound of formula V where both are $R_8$ groups are carbonyl and not protected carbonyl groups. This reaction is carried out in the same manner hereinbefore described in connection with the reaction of the compound of formula III with the compound of IV to produce the compound of formula I.

The compound of formula X is converted to the compound of formula XI by reduction in an anhydrous medium. This reaction is carried out in the same manner as hereinbefore described in connection with the conversion of the compound of formula V to the compound VI. In producing the compound of formula I from the compound of formula X, the compound of formula XI is reacted with the compound of formula VIII in the same manner as described in connection with the reaction of the compound of formula VI with the compound of formula VIII to produce the compound of formula VII. Depending upon which $R_{15}$ group is desired, a compound of formula VIII-A, VIII-B, VIII-C or VIII-D can be utilized in this reaction. In this reaction, corresponding compound of formula I is formed with both thio group substituted with $R_{15}$. However, this disubstituted thio compound forms in only a small amount and may be separated from the compound of formula I by conventional separation methods such column chromatography.

In accordance with this invention the compound of formula I can be prepared by reacting the compound of formula X with a Gringnard or alkyl lithium form of the compound of formula VIII-B where x and z are O. This reaction is carried out by conventional means to produce the compound of formula I where 1 of $R_5$ or $R_5'$ is

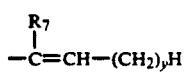

where $R_7$ and y are as above.

In accordance with another embodiment of this invention, the compound of formula I can be prepared from the compound of formula III via the following intermediate:

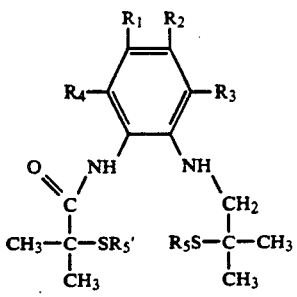

XII wherein $R_1$, $R_2$, $R_3$, $R_4$, $R_5$ and $R_5'$ are as above.

In forming the compound of formula XII, the compound of formula III is reacted with a compound of the formula

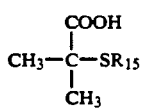

XIII wherein $R_{15}$ is as above.

The compound of formula III is reacted with the compound of formula XIII to form the amide of formula XII. Any conventional method of condensing an amine with a carboxylic acid to form an amide, can be utilized to carry out this reaction. Generally, this amine condensation with an acid can be carried out by reacting the amine of formula III with a reactive derivative of an acid of formula XIII such as the halo derivative of this acid. Any conventional method of converting an acid into an acid chloride, such as by reacting the acid of formula XIII with thionyl chloride, can be utilized in forming the acid halide of the compound of formula XIII. The reactive derivative of the compound of formula XIII is condensed with the compound of formula III to prepare the compound of formula XII utilizing any conventional method of reacting an amine and an acid chloride to form an amide.

The compound of formula XII can be converted to the compound of formula I by reduction with a hydride reducing agent. Any conventional hydride reducing agent can be utilized in this conversion. Among the preferred hydride reducing agents are lithium aluminum hydride. The use of a hydride reducing agent such as lithium aluminum hydride only reduces the carbonyl group without affecting any double or triple bonds within the molecule of the compound of formula XII. Any of the conditions conventional for hydride reduction can be used in carrying out this reduction.

The compound of formula XIII is formed from a compound of the formula:

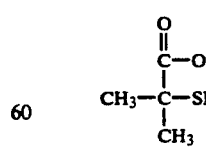

by condensing with the halide of formula VIII. Depending on the particular $R_{15}$ substituent desired, a compound of formula VIII-A, VIII-B, VIII-C or VIII-D is be utilized in this condensation. This condensation takes place in the same manner as described in connection with the condensation of the compound of formula VI with the compound of formula VIII to produce the compound of formula VII.

The complex which can be utilized in imaging organs particularly the brain is formed by reacting the compound of formula I with the salt of a radioactive metal. Any conventional salt of the aforementioned radioactive metals can be utilized in forming the complex. If one wishes to form the radioactive technetium complex of the compound of formula I, one can react technetium-99m pertechnetate with the compound of formula I in the presence of a reducing agent such as a stannous reducing agent particularly stannous chloride. On the other hand, radiolabelling can be carried out with other conventional salts of radioactive metals such as indium, technetium, gallium and ruthenium. Among the other salts are the acetate, citrate and halide salts, such as the chloride, bromide, fluoride and iodide salts. The reaction to form the complex is carried out by simply mixing radioactive metal salts with a compound of formula I. This reaction can be carried out in a solvent medium preferably an aqueous media at room temperature. In carrying out this reaction, temperature and pressure are not critical. Thus reaction can be carried out at room temperature and atmospheric pressure.

The complexes formed by reacting the compound of formula I, with technetium-99m pertechnetate and a reducing agent such as stannous chloride has the following formula

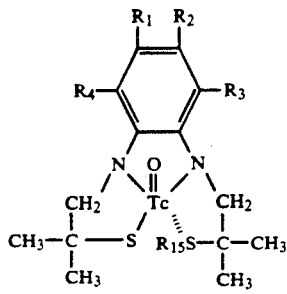

XX where $R_1$, $R_2$, $R_3$, $R_4$, and $R_{15}$ are as above.

The radioactive metal complex prepared from the compound of formula I may be administered intravenously in any conventional medium by intravenous injection, such as an aqueous saline medium, or in a blood plasma medium. Such medium may also contain conventional pharmaceutical adjuvant materials such as, for example, pharmaceutically acceptable salts to adjust the osmotic pressure, buffers, preservatives and the like. Among the preferred mediums are plasma and normal saline containing a solubilizer suitable for intravenous injection such as 2-hydroxypropyl-$\beta$-cyclodextrin.

Radiolabelling the compound of formula I to form the radioactive complex can be carried out by conventional means sucha s described above. The radioactive metal complex of this invention can be injected intravenously into a patient for diagnostic imaging of all conventional organs of the body, i.e. lung, heart, liver, kidney, brain, etc. In accordance with this invention, the radioactive metal complex of formula I is administered in a single unit injectable dose. Any of the common carriers, such as sterile saline solution, plasma, etc. can be used for preparing the injectable solution for use to diagnostically image in accordances with this invention. Generally, the unit dose to be administered contains radioactivity of about 3.0 mCi to about 30 mCi, preferably 10 mCi to about 20 mCi. The solution to be injected is in a unit dosage form of about from 0.1 milliliters to about 10 milliliters preferably from about 1 to about 5 milliliters. After intravenous administration, the radioactive metal complex of formula I will image the organs in vivo. Any conventional method of visualizing or imaging for diagnostic purposes can be utilized in accordance with this invention.

In accordance with this invention, the radioactive complex can be distributed in a saline or plasma medium or the compound of formula I can be utilized and the radioactive complex formed in situ prior to injection by mixing the compound of formula I above with a radioactive metal to form the complex just prior to administration. On the other hand, a kit can be utilized which contains a certain quantity of the compound of formula I and a suitable reducing agent such as stannous chloride, and a suitable solubilizer such as 2-hydroxypropyl-$\beta$-cyclodextrin. In addition the kit may contain ascorbic acid for stabilizing the complex once it is formed and a corresponding quantity of a salt of a radioactive material for forming the complex in situ prior to injection. On the other hand this radioactive salt can be independently furnished to the hospital or radiopharmacy.

The invention is further illustrated by the following examples, which are not intended to limit the invention.

EXAMPLE 1

2-Amino-1-(2-mercapto-2-methylpropylamino)benzene o-Phenylenediamine (15.31 g, $1.42 \times 10^{-1}$ mol, 100 M%) and 12.46 g ($1.42 \times 10^{-1}$ mol, 100 M%) isobutylene sulfide (Synder et al, J. Am. Chem. Soc. 69: 2672-2674, 1947) were mixed in a Parr bomb and heated in an oven at 80° C. for 18 hr. The bomb was cooled to room temperature and then opened. The crude brown oil contained some solid. The mixture was dissolved in 150 ml ether (some white solid did not dissolve), washed with saturated aqueous NaCl solution, and the solvent was removed on the rotary evaporator. The oily residue was placed on flash silic in a 600 ml sintered glass funnel and eluted with 500 ml portion of hexane, 90% hexane/ether, twice with 80% hexane/ether and twice with 50% hexane/ether. Evaporation of the first 50:50 hexane/ether fraction gave 7.36 g (26.5%) of 2-amino-1-(2-mercapto-2-methylpropylamino)benzene as a waxy crystalline product, mp 38°-40° C.

EXAMPLE 2

2-(2-Mercapto-2-methylpropylamino)-1-[4-pentenylthio)-2-methylpropylamino]benzene 2-Amino-1-(2-mercapto-2-methylpropylamino)benzene (0.155 g, $7/9 \times 10^{-4}$ mol) and 0.30 g ($1.74 \times 10^{-3}$ mol, 220 M%) of 2-(4-pentenylthio)-2-methylpropanal were dissolved in 40 ml methanol. Acetic acid (0.09 ml, $1.59 \times 10^{-3}$ mol, 200 M%) was added followed by 0.155 g ($2.3 \times 10^{-3}$ mol, 300 M%) sodium cyanoborohydride. The reaction was stirred at room temperature under nitrogen for 17 hr, then 20 ml 0.5M HCl was added and the mixture was extracted with 2×40 ml diethyl ether. The ether layer was washed with 30 ml saturated NaCl solution and dried (Na$_2$SO$_4$), and the solvent was removed on the rotary evaporator. The product was purified by radial chromatography on a 2 mm silica plate eluting with 50 ml 100% hexane and 100 ml 90% hexane/ether to give 0.27 g (97% yield) of 2-(2-mercapto-2- methylpropylamino)-1-[2-(4-pentenylthio)-2-methylpropylamino]-benzene as an oil.

EXAMPLE 3

2,2'-Dithio-bis(2-methylpropanal)bis-ethylenedioxy acetal 2,2'-Dithio-bis(2-methylpropanal) (4.12 g, $2.00 \times 10^{-2}$ mol, 100 M%) and ethylene glycol (5.00 ml, $8.97 \times 10^{-2}$ mol, 448 M%) were placed in a 250 ml round-bottom flask containing 30 ml benzene and 0.0463 g ($2.43 \times 10^{-4}$ mol, 1.2 M%) p-toluenesulfonic acid monohydrate. The reaction flask was equipped with a Dean-Stark trap and heated to reflux for 6 hours, when the theoretical amount of water had collected in the Dean-Stark trap. The reaction was stirred at 21° C. for 16 hr, then poured into 50 ml diethyl ether and washed with 30 ml 0.5M NaOH. The ether layer was washed with 20 ml saturated sodium chloride, dried over MgSO$_4$, filtered, and the solvent was removed on the rotary evaporator to afford 5.51 g 2,2'-dithio-bis(2-methylpropanal)bis-ethylenedioxy acetal (94% yield).

EXAMPLE 4

2-Mercapto-2-methylpropanalethylenedioxy acetal 2,2-Dithio-bis (2-methylpropanal)bis-ethylenedioxy acetal, (2.40 g, $8.16 \times 10^{-3}$ mol, 100 M%) was placed in a 250 ml round-bottom flask equipped with a dry ice-/acetone cold finger. The reaction flask and cold finger were cooled with dry ice and acetone. Ammonia gas was condensed by the cold finger and dripped into the reaction flask until 40 ml liquid ammonia was in the round-bottom flask. Small balls of hexane-washed sodium metal were added one at time, causing the reaction mixture to turn blue. Tetrahydrofuran (20 ml) was added after 30 min to help dissolve the insoluble starting material. The blue solution rapidly became colorless upon addition of the freshly distilled tetrahydrofuran. The glassy starting material slowly dissolved as the sodium metal was added. After 3.5 hr all of the starting material was dissolved and the reaction solution remained blue when sodium was added. Solid ammonium chloride was added, causing the reaction to change from blue to colorless. The flask was then removed from the dry ice-acetone bath and placed in a 40° C. warm water bath to evaporate the ammonia. The crude solid reaction mixture was dissolved in 100 ml water and concentrated phosphoric acid was added until the solution was pH 2. The aqueous solution was extracted with $2 \times 100$ ml diethyl ether. The ether layers were combined, washed with 50 ml saturated sodium chloride, and dried over sodium sulfate. The solvent was removed on the rotary evaporate to obtain 2.34 g (97% yield) of 2-mercapto-2-methylpropanalethylenedioxy acetal as an oily product with a strong smell. TLC (1:1 ether/hexanes) Rf 0.66.

EXAMPLE 5

2-(4-pentenylthio)-2-methylpropanalethylenedioxy acetal

2-Mercapto-2-methylpropanalethylenedioxy acetal (3 g, $2.0 \times 10^{-2}$ mol) was dissolved in 50 ml tetrahydrofuran (freshly distilled over sodium). Sodium hydride (50% mineral oil dispersion washed with $3 \times 5$ ml portions of hexane) (1.15 g, $2.42 \times 10^{-2}$ mol, 120 M%) was then added. The mixture was stirred under nitrogen for 10 minutes, followed by the addition of 2.62 ml, ($2.43 \times 10^{-2}$ mol, 110 M%) 5-bromo-1-pentene. The mixture was stirred under nitrogen for 18 hours, then 10 ml methanol was added slowly, 100 ml H$_2$O was added, and the mixture was extracted with $2 \times 100$ ml diethyl ether. The combined ether extracts were washed with saturated NaCl, dried over anhydrous Na$_2$SO$_4$, and the solvent was removed on the rotary evaporator to give 4.5 g (99% yield) of 2-(4-pentenylthio)-2-methylpropanalethylenedioxy acetal as a yellow oil.

EXAMPLE 6

2-(4-Pentenylthio)-2-methylpropanal 2-(4-Pentenylthio)2-methylpropanalethylenedioxy acetal, (4.5 g, $2.06 \times 10^{-2}$ mol) was dissolved in 25 ml tetrahydrofuran, then 25 ml 0.5M HCl was added, and the mixture was heated to reflux for 3 hours. The cooled reaction mixture was treated with 100 ml H$_2$O, and the aqueous layer was extracted with $2 \times 100$ ml portions of diethyl ether. The combined ether layers were washed with 100 ml saturated NaCl, and dried over anhydrous Na$_2$SO$_4$. Rotary evaporation yielded 2.9 g (82% yield) of 2-(4-opentenylthio)-2-methylpropanal as a yellow oil.

EXAMPLE 7

Tc-99m complex of 2-(2-Mercapto-2-methylpropylamino)-1-[2-pentenylthio)-2-methylpropylamino] benzene.

2-(2-Mercapto-2-methylpropylamino)1-[2-(4-pentenylthio)-2-methylpropylamino]benzene (0.25-5 mg) was dissolved in 3 ml 50% ethanol/water containing 0.5-80 mCi NaTcO$_4$ Tc-99m. Nitrogen gas was bubbled through the solution for 3 minutes, then stannour chloride (0.001-0.2 ml, containing $1 \times 10^{-8}$ to $2.0 \times 10^{-6}$ mol) was added to the solution to produce the Tc-99m complex of 2-(2-mercapto-2-methylpropylamino)-1-[2-(4-pentenylthio)-2-methylpropylamino]benzene. The purity of the complex was then measured by TLC and HPLC. HPLC (9:1 ethanol/H$_2$O, 1.5 ml/min, Waters Radial-Pak (C18) Rt. 3.78 min, radiochemical purity 100%. TLC (ethyl acetate/methanol/water/15 M NH$_4$OH-86:10:3:1, Rf 0.92, radiochemical purity 97%. Electrophoresis (0.5M NaH$_2$PO$_4$, pH 4.5, 300 volts, 45 min) neutral.

EXAMPLE 8

2-(trans-2-Butenylthio)-2-methylpropanalethylenedioxy acetal

2-Mercapto-2-methylpropanalethylenedioxy acetal, (2.15 g, $1.45 \times 10^{-2}$ mol, 100 M%) was dissolved in 130 ml tetrahydrofuran. Hexane-washed sodium hydride (50% in oil) 0.77 g ($1.60 \times 10^{-2}$ mol, 110 M%) was added to the reaction solution. Crotyl bromide (1.64 ml, $1.60 \times 10^{-2}$ mol, 110 M%) was added to the reaction solution which was then stirred at 21° C. for 19 hr before adding 60 ml H$_2$O. The reaction mixture was extracted with $2 \times 60$ ml ether. The organic extracts were combined, washed with 40 ml saturated NaCl solution and dried with Na$_2$SO$_4$. The ether was removed on the rotary evaporator to afford 2.80 g (95% yield) of 2-(trans-2-butenylthio)-2-methylpropanal-ethylenedioxy acetal as an oil.

EXAMPLE 9

2-(trans-2-Butenylthio)-2-methylpropanal 2-(trans-2-Butenylthio)-2-methylpropanalethylenedioxy acetal (2.56 g, $1.27 \times 10^{-2}$ mol, 100 M%) was placed in a mixture of 40 ml tetrahydrofuran and 100 ml 0.5M HCl. The solution was heated at reflux for 2 hr and then extracted with 2×40 ml diethyl ether. The organic extracts were combined, washed with 40 ml saturated aqueous NaCl solution, and dried ($Na_2SO_4$). The solvent was removed on the rotary evaporator to afford 1.94 g (96.7% yield) 2-(trans-2-butenylthio)-2-methylpropanal as an oil.

EXAMPLE 10

1-[2-(trans-2-Butenylthio)-2-methylpropylamino]-2-(2-mercapto-2-methylpropylamino)benzene 2-Amino-1-(2-mercapto-2-methylpropylamino)benzene (0.36 g, $1.84 \times 10^{-3}$ mol) and 0.58 g ($3.67 \times 10^{-3}$ mol, 200 M%) 2-(trans-2-butenylthio)-2-methylpropanal were reacted by the procedures in Example 2 to give 0.55 g (88% yield) 1-[2-(trans-2-Butenylthio)-2-methylpropylamino]-2-(2-mercapto-2-methylpropylamino)benzene as an oil after purification by radial chromatography on a 4 mm silica plate eluting with 100% hexane.

EXAMPLE 11

Tc-99m complex of 1-[2-(trans-2-Butenylthio)-2-methylpropylamino]-2-(2-mercapto-2-methylpropylamino) benzene 1-(2-trans-2-Butenylthio)-2-methylpropylamino)-2-(2-mercapto-2-methylpropylamino) benzene was reacted with Tc-99m sodium pertechnetate by the procedure of Example 7 to produce the Tc-99m complex of 1-[2-(trans-2-butenylthio)-2-methylpropylamino]-2-(2-mercapto-2-methylpropylamino) benzene. HPLC (90% ethanol//H$_2$O, 1.5 ml/min, Waters Radial-Pak C-18) Rt 4.06 min, radiochemical purity 100%. TLC (70% hexane/diethyl ether) RF 0.26, radiochemical purity 94%. Electrophoresis (0.05M NaH$_2$PO$_4$, pH 4.5, 300 volts, 45 min) neutral.

EXAMPLE 12

2-Allylthio-2-methylpropanalethylenedioxy acetal

2-Mercapto-2-methylpropanalethylenedioxy acetal (10 g, $6.7 \times 10^{-2}$ mol, 100 M%) was dissolved in 150 ml tetrahydrofuran (distilled over sodium). Hexane-washed sodium hydride (3.86 g, $8 \times 10^{-2}$ mol, 120 M%) (50% in oil) was added to the solution. Allyl bromide (5.80 ml, $6.71 \times 10^{-2}$ mol, 100 M%) was then added, and the mixture stirred at room temperature for 18 hours. Methanol (50 ml) was added and the mixture was extracted with 2×100 ml diethyl ether. The combined ether layers were then washed with 100 ml saturated NaCl and dried over anhydrous Na$_2$SO$_4$. The ether was removed on a rotary evaporator to yield 12.05 g (95% yield) of 2-allylthio-2-methylpropanalethylenedioxy acetal as a yellow oil.

EXAMPLE 13

2-Allylthio-2-methylpropanal 2-allylthio-2-methylpropanalethylenedioxy acetal (12.50 g, $6.4 \times 10^{-2}$ mol) was heated at reflux for 5 hours in a mixture of 100 ml tetrahydrofuran and 50 ml 0.15M HCl. Thereafter, the aqueous layer was extracted with 2×100 ml diethyl ether. The combined organic extracts were then washed with 100 ml saturated NaCl and dried over anhydrous Na$_2$SO$_4$. The solvent was removed on a rotary evaporator to give 7.10 g (77% yield) of 2-allylthio-2-methylpropanal as a yellow oil.

EXAMPLE 14

1-(2-Allylthio-2-methylpropylamino)-2-(2-Mercapto-2-methylpropylamino)-benzene

2-Amino-1-(2-mercapto-2-methylpropylamino)benzene (3.5 g, $1.78 \times 10^{-2}$ mol) and 2-(allylthio)-2-methylpropanal (3.85 g, $2.67 \times 10^{-2}$ mol, 150 M%) were dissolved in 200 ml methanol. Glacial acetic acid (2.05 ml, $3.56 \times 10^{-2}$, 200 M%) and sodium cyanoborohydride (3.36 g, $5.35 \times 10^{-2}$ mol, 300 M%) were then added. The reaction was stirred at room temperature for 18 hr, then 100 ml 0.5M HCl was added and the mixture was extracted with 2×100 ml diethyl ether. The combined organic extracts were washed with 100 ml saturated NaHCO$_3$, then with 100 ml saturated NaCl. The ether layer was dried over anhydrous Na$_2$SO$_4$, and the solvent was removed on the rotary evaporator. The crude product (6.7 g) was purified by filtration through a 600 ml sintered glass funnel filled silica bed, using 95% hexane/diethyl ether as the eluting solvent to give 4 g (70% yield) of 1-(2-allylthio-2-methylpropylamino)-2-(2-mercapto-2-methylpropylamino]benzene as a yellow oil.

EXAMPLE 15

Tc-99m complex of 1-(2-Allylthio-2-methylpropylamino]-2-(2-mercapto-2-methylpropylamino) benzene 1-[2-Allythio-2-methylpropylamino]-2-mercapto-2-methylpropylamino) benzene was reacted with Tc-99m sodium pertechnetate by the method of Example 7. HPLC (90% ethanol:H$_2$O, 1.5 ml/min, C18 5 micron Nova Pak) 3.58 min (97%). TLC (50% diethyl ether: chloroform) RF 0.73, radiochemical purity 96%. Electrophoresis (0.05 M NaH$_2$PO$_4$, pH 4.5, 300 volts, 30 min) neutral.

EXAMPLE 16

2-[3-Butenylthio]-2-methylpropanalethylenedioxy acetal

2-Mercapto-2-methylpropanalethylenedioxy acetal (7 g, $4.69 \times 10^{-2}$ mol) was dissolved in 100 ml tetrahydrofuran (distilled over sodium). Hexane-washed sodium hydride (2.70 g, $5.62 \times 10^{-2}$ mol) (50% in mineral oil) and 4-bromo-1-butene (4.80 ml, $4.60 \times 10^{-2}$ mol, 100 M%) were then added, and the mixture was stirred at room temperature for 18 hours. Methanol (50 ml) was then added, and the reaction mixture was extracted with 2×100 ml diethyl ether. The combined organic extracts were washed with 100 ml saturated NaCl and dried over anhydrous Na$_2$SO$_4$. The ether was removed on a rotary evaporator to yield 9.0 g (94% yield) of 2-[3-butenylthio]-2-methylpropanalethylenedioxy acetal.

EXAMPLE 17

2-[3-Butenylthio]-2-methylpropanal

2-[3-Butenylthio]-2-methylpropanalethylenedioxy acetal (9.0 g, $4.43 \times 10^{-2}$ mol) was placed in a mixture of 100 ml tetrahydrofuran and 100 ml 0.5M HCl. The solution was heated to reflux for 4 hours, then the aqueous layer was extracted with 2×100 ml diethyl ether. The combined etheral layers were washed with 100 ml saturated NaCl and dried over anhydrous Na$_2$SO$_4$. The solvent was removed on the rotary evaporator to give 6.3 g (90% yield) of 2-[3-butenylthio]-2-methylpropanal as a yellow oil.

EXAMPLE 18

1-[2-(3-Butenylthio)-2-methylpropylamino]-2-(2-mercapto-2-methylpropylamino)benzene 2-Amino-1-(2-mercapto-2-methylpropylamino)benzene (3.5 g, $1.78 \times 10^{-2}$ mol, 100 M%) and 2-(3-butenylthio)-2-methylpropanal (4.23 g, $2.67 \times 10^{-2}$ mol, 150 M%) were dissolved in 200 ml methanol. Glacial acetic acid (2.05 ml, $3.56 \times 10^{-2}$ mol, 200 M%) and sodium cyanoborohydride (3.36 g, $5.35 \times 10^{-2}$ mol, 300 M%) were then added. After 17 hours, the reaction was quenched by the addition of 100 ml 0.5 N HCl. The acidic solution was then extracted with $2 \times 100$ ml diethyl ether. The combined organic extracts were washed with 100 ml saturated $NaHCO_3$, followed by 100 ml saturated NaCl. The ether layer was then dried over anhydrous $Na_2SO_4$. The solvent was removed on the rotary evaporator, and the residue was purified by filtration through a 600 ml sintered-glass funnel silica bed, using 90% hexane/diethyl ether as the eluting solvent, to give 5 g (84% yield) 1-[2-(3-butenylthio)-2-methylpropylamino]-2-(2-mercapto-2-methylpropylamino)-benzene as a yellow oil.

EXAMPLE 19

Tc-99m complex of
1-[2-(3-Butenylthio)-2-methylpropylamino-2-(2-mercapto-2-methylpropylamino)benzene 1-[2-(3-Butenylthio)-2-methylpropylamino]-2-(2-mercapto-2-methylpropylamino)benzene was reacted with Tc-99m sodium pertechnetate by the method of Example 7 to produce the Tc-99m complex of 1-[2-(3-butenylthio)-2-methylpropylamino]-2-(2-mercapto-2-methylpropylamino)benzene. HPLC (90% ethanol:$H_2O$, 1.5 ml/min, C18 5 micron Nova Pak) 3.86 min (96%). TLC (80% ethyl acetate:petroleum ether) Rf 0.45, radiochemical purity 95%.

EXAMPLE 20

2-(Propylthio)-2-methylpropanalethylenedioxy acetal

In a 100 ml round-bottom flask equipped with a nitrogen inlet and magnetic stir bar, 2-mercapto-2-methylpropanalethylenedioxy acetal, (1.53 g, $1.03 \times 10^{-2}$ mol, 100 M%) and iodopropane (1.93 g, $1.14 \times 10^{-2}$ mol, 110 M%) were combined in 50 ml of freshly distilled tetrahydrofuran under nitrogen. Sodium hydride (0.27 g, $1.14 \times 10^{-2}$ mol, 110 M%) (50% mineral oil dispersion washed $3 \times$ with 20 ml petroleum ether) was added to the reaction flask, causing gas evolution. The mixture was stirred at 25° C. for 2 hr and was then quenched with 50 ml 0.5M NaOH. The mixture was extracted with $3 \times 50$ ml diethyl ether. The combined ether layers were washed with $2 \times 40$ ml NaCl and were dried over anhydrous $Na_2SO_4$. Removal of the solvent by rotary evaporation gave 2.10 g (100% yield) of 2-(propylthio)-2-methylpropanalethylenedioxy acetal as a colorless liquid.

EXAMPLE 21

2-Propylthio-2-methylpropanal

In a 250 ml round-bottomed flask equipped with a reflux condenser and nitrogen inlet, 2-(propylthio)-2-methylpropaneddioxy acetal (2.00 g, $1.05 \times 10^{-2}$ mol, 100 M%) was dissolved in 25 ml tetrahydrofuran and 25 ml 0.5M HCl. The mixture was heated to reflux for 2 hr. After cooling to room temperature, the solution was extracted with $3 \times 50$ ml diethyl ether. The combined ether layers were washed with 50 ml $H_2O$, 50 ml saturated NaCl, and were dried over anhydrous $Na_2SO_4$. Filtration and removal of the solvent by rotary evaporation provided 1.37 g (89% yield) of 2-propylthio-2-methylpropanal as a colorless liquid.

EXAMPLE 22

2-(2-Mercapto-2-methylpropylamino)-1-[2-propylthio-2-methylpropylamino]benzene

2-Amino-1-(2-mercapto-2-methylpropylamino)benzene (0.40 g, $2.06 \times 10^{-3}$ mol) and 0.452 g ($3.09 \times 10^{-3}$ mol, 150 M%) of 2-propylthio-2-methylpropanal were reacted by the method of Example 2 to give 0.239 g (40% yield) of 2-(2-mercapto-2-methylpropylamino)-1-[2-propylthio-2-methylpropylamino]-benzene as a colorless oil after purification by radial chromatography on a 4 mm silica gel plate eluting with 200 ml 5% diethyl ether/petroleum ether and 100 ml 7% diethy ether/petroleum ether.

EXAMPLE 23

Tc-99m Complex of
2-(2-Mercapto-2-methylpropylamino)-1-[2-propylthio-2-methylpropylamino]-benzene 2-(2-Mercapto-2-methylpropylamino)-1-(2-propylthio-2-methylpropylamino)benzene was reacted as in Example 7 to produce the Tc-99m complex of 2-(2-mercapto-2-methylpropylamino)-1-[2-propylthio-2-methylpropylamino]-benzene. Two main components were present in the reaction solution. The mixture was purified by injecting 200 l of the reaction mixture into the HPLC and collecting fractions. The third fraction contained the desired Tc-99m complex (1.0 mCi/ml). HPLC (90% ethanol/$H_2O$, 1.5 ml/min, Waters Radial-Pak C18) Rt 3.66 min, radiochemical purity 100%. TLC (30% ethyl acetate/hexane) Rf 0.63, radiochemical purity 94%. Partition coefficient (1-octanol/0.1M phosphate buffer pH 7.4) 33.

EXAMPLE 24

2-(2-Propynylthio)-2-methylpropanalethylenedioxy acetal

2-Mercapto-2-methylpropanalethylenedioxy acetal, (14.80 g, $1.00 \times 10^{-1}$ mol, 100 M%) was dissolved in 100 ml tetrahydrofuran. Propargyl chloride (8.06 ml, $1.00 \times 10^{-1}$ mol, 100 M%) and 4.80 g ($1.2 \times 10^{-1}$ mol, 120 M%) sodium hydroxide dissolved in 10 ml water were added to the reaction solution. The solution was stirred at 21° C. for 24 hr. Water (60 ml) was added and the reaction solution was extracted with $2 \times 70$ ml ether. The ether layers were combined, washed with 60 ml saturated sodium chloride, and dried over sodium sulfate. The solvent was removed on the rotary evaporator to give a crude oily product which was then distilled under vacuum (bp 80°-81° C., 0.09 mmHg) to afford 12.60 g (68% yield) of 2-(2-propynylthio)-2-methylpropanalethylenedioxy acetal as a colorless oil.

EXAMPLE 25

2-(2-Propynylthio)-2-methylpropanal 2-(2-Propynylthio)-2-methylpropanalethylenedioxy acetal, (4.59 g, $2.47 \times 10^{-2}$ mol, 100 M%) was dissolved in a mixture of 30 ml tetrahydrofuran and 30 mnl 0.5M HCl. The solution was heated at reflux for 4 hr, cooled, and then extracted with 2×75 ml diethyl ether. The ether layers were combined, washed with 40 ml of saturated sodium chloride solution, and dried (Na$_2$SO$_4$). The solvent was removed under on the rotary evaporator to afford 2-(2-propynylthio)-2-methylpropanal 3.26 g (93% yield) as an oily product.

EXAMPLE 26

2-(2-Mercapto-2-methylpropylamino)-1-[2-(2-propynylthio)-2-methylpropylamino]benzene 2-Amino-1-(2-mercapto-2-methylpropylamino)benzene (5.59 g, 2.85×10$^{-2}$ mol) and 2-(2-propynylthio)-2-methylpropanal (6.07 g, 4.28×10$^{-2}$ mol, 150 M%) were mixed, then 125 ml methanol and 5.27 ml (5.7×10$^{-2}$ mol, 200 M%) acetic acid were added and solids were allowed to dissolve. Sodium cyanoborohydride (5.39 g, 8.56×10$^{-2}$ mol, 300 M%) was added to the reaction solution in three equal portions. The reaction was stirred at 21° C. for 17 hr, then quenched with 100 ml 0.5M HCl, stirred for 15 min, and then extracted with 2×150 ml ether. The ether layers were combined, washed with 60 ml saturated NaCl solution and dried over Na$_2$SO$_4$. The solvent was removed on the rotary evaporator and the residue was purified by filtration through flash silica in a 600 ml sintered glass funnel ¾ full of silica, eluting with 500 ml portions of 2×hexane and 2×90% hexane/ether to produce 6.88 g (75% yield) 2-(2-mercapto-2-methyl-propylamino)-1-[2-(2-propynylthio)-2-methylpropylamino]-benzene.

EXAMPLE 27

Tc-99m Complex of 2-(2-Mercapto-2-methylpropylamino)-1-[2-(2-propynylthio)-2-methylpropylamino]benzene 2-(2-Mercapto-2-methylpropylamino)-1-(2-propynylthio)-2-methylpropylamino)-benzene was reacted with Tc-99m sodium pertechnetate by the method of Example 7 to produce the Tc-99m complex of 2-(2-mercapto-2-methylpropylamino)-1-[2-(2-propynylthio)-2-methylpropylamino]benzene. The complex was purified by filtration through a 0.22 micron Millex GS filter. HPLC (90% ethanol/H$_2$O, 1.5 ml/min, Waters Radial-Pak C18) Et 3.33 min, radiochemical purity 100%. TLC (70% hexane/ethyl acetate, Rf 0.43, radiochemical purity 93%. Electrophoresis (0.05M NaH$_2$PO$_4$, pH 4.5, 300 volts, 30 min) neutral.

EXAMPLE 28

2-Ethylthio-2-methylpropanalethylenedioxy acetal

2-Mercapto-2-methylpropanalethylenedioxy acetal (1.99 g, 1.34×10$^{-2}$ mol, 100 M%) and iodoethane (2.31 g, 1.48×10$^{-2}$ mol, 110 M%) were treated with sodium hydride (0.35 g, 1.48×10$^{-2}$ mol, 110 M%) in tetrahydrofuran (40 ml) for 4 hr as described for Example 20. Extraction and solvent removal provided 2.88 g (100% yield) of 2-ethylthio-2-methylpropanalethylenedioxy acetal as a colorless liquid.

EXAMPLE 29

2-Ethylthio-2-methylpropanal 2-(Ethylthio)-2-methylpropanalethylenedioxy acetal, (2.88 g, 1.6×10$^{-2}$ mol) was heated for 2.5 hr in 0.5M HCl (25 ml) and tetrahydrofuran (25 ml) and isolated as described in Example 21 to give 2-ethylthio-2-methylpropanal, 2.31 g (100% yield) as a yellow liquid containing traces of tetrahydrofuran.

EXAMPLE 30

1,2,3,6,7,8-Hexahydro-3,3,6,6,-tetramethyl-4,5,1,8-benzodithiadiazacyclodecine o-Phenylenediamine (1.0 g, 1.00×10$^{-2}$ mol, 100 M%) was dissolved in a solution containing (2.06 g, 1.00×10$^{-2}$ mol, 100% M%) 2,2'-dithio-bis (2-methylpropanal) in 30 ml methanol. Sodium cyanoborohydride (1.89 g, 3.00×10$^{-2}$ mol, 300 M%) was added to the 21° C. reaction solution. Acetic acid was added dropwise until the pH of the reaction solution was pH 5.5 (pH paper), then the reaction was stirred under argon for 15 hr at 21° C. The reaction solution was poured into 200 ml 0.5M HCl. The solution got cloudy and a soft brown lump formed. The lump was removed with a glass stirring rod and the acid solution was basified (with cooling) with sodium hydroxide pellets to pH 13. The basified solution was extracted with 2×100 ml portions of ether. The ether layers were combined and washed with 50 ml saturated sodium chloride solution. The layer was dried (Na$_2$SO$_4$), filtered, and the solvent was evaporated to afford 1.4 g of crude product oil. The crude product was dissolved in chloroform and absorbed onto 5 g silica gel. The chloroform was removed on the rotary evaporator, leaving free flowing silica, which was poured into a 60 ml sintered glass ¾ full of flash silica (Merck silica gel 60, 230–400 mesh, 0.040–0.063 mm). The silica was washed with 200 ml 5:25 hexanes/ether and upon rotary evaportion yielded 0.69 g (24.5% yield) of 1,2,3,6,7,8-Hexahydro-3,3,6,6-tetramethyl-4,5,1,8-benzodithiadiazacyclodecine as a solid.

EXAMPLE 31

1,2-Bis(2-mercapto-2-methylpropylamino)benzene 1,2,3,6,7,8-Hexahydro-3,3,6,6-tetramethyl-4,5,1,8-benzodithiadiazacyclodecine (51.0 mg, 1.81 mmol) was placed in a 100 ml round-bottom flask. Liquid NH$_3$ (30 ml), condensed in a dry ice-acetone bath, was added to the mixture. The suspension was stirred and 4–5 pieces of sodium metal was added which caused the reaction to become a deep blue color. After 2 hours, stirring, 0.5 g ammonium chloride was added. The resulting colorless solution was boiled to dryness at room temperature. Water (30 ml) was added dissolving the white precipitate and the mixture was extracted 2×100 ml with diethyl ether. The ether layers were combined, washed with saturated NaCl, dried with anhydrous Na$_2$SO$_4$, filtered, and removed on the rotary evaporator. The crude product was purified in a flash column (14×7 cm silica gel 60) using 1:1 chloroform/diethyl ether as the eluting solvent. The solvent of the desired fraction was removed on the rotary evaporator and the residue was dried in a vacuum dessicator to afford 0.28 g (37% yield) 1,2-bis(2-mercapto-2-methylpropylamino)benzene as an oil.

EXAMPLE 32

2-(2-Mercapto-2-methylpropylamino)-1-[2-ethylthio-2-methylpropylamino]benzene

In a 50 ml round-bottom flask, 1,2-bis(2-mercapto-2-methylpropylamino)benzene (397 mg, 1.40 mmol) was dissolved in 25 ml of tetrahydrofuran (freshly distilled from Na with benzophenone). The solution was flushed with nitrogen for 5-10 min, and sodium hydride (40 mg, 1.55 mmol, 120 M%) [50% mineral oil dispersion washed 3×10 ml petroleum ether] was added to the reaction flask causing gas evolution. After 10-15 min, ethyl iodide (196 mg, 1.26 mmol, 90 M%) was added dropwise by syringe. The mixture was allowed to stir for 40 min, during which time a fine white precipitate formed. TLC indicated a new product with higher Rf. Five ml 0.5M HCl was added, the solution was transferred to a separatory containing 50 ml 0.5M HCl and the mixture was extracted with 3×50 ml ether. The combined ether layers were washed with 50 ml 0.5 M NaOH, 50 ml saturated NaCl and were dried over anhydrous Na$_2$SO$_4$. Removal of the solvent by rotary evaporation provided 315 mg (72%) of an oil. The crude product was purified by radial chromatography using a 2 mm silica gel plate and 100 ml petroleum ether, 100 ml 2% diethyl ether/petroleum ether, 2×100 ml 5% diethyl ether/petroleum ether to elute the product. The fractions containing the mono-alkylated product were combined and concentrated to give 246 mg (56% of 2-(2-mercapto-2-methylpropylamino)-1-[2-ethylthio-2-methylpropylamino] benzene as a white solid.

EXAMPLE 33

2-(2-Mercapto-2-methylpropylamino)-1-[2-ethylthio-2-methylpropylamino]-benzene

2-Amino-1-(2-mercapto-2-methylpropylamino)benzene (0.433 g, 2.23×10$^{-3}$ mol) and 0.599 g (4.46×10$^{-3}$ mol, 200 M%) 2-ethylthio-2-methylpropanal were reacted by the method of Example 2 to give 0.307 (28% yield) of 2-(2-mercapto-2-methylpropylamino)-1-[2-ethylthio-2-methylpropylamino] benzene as a colorless oil after purification by radial chromatography on a 4 mm silica gel plate eluting with 300 ml 5% diethyl ether/petroleum ether.

EXAMPLE 34

Tc-99m complex of 2-(2-Mercapto-2-methylpropylamino)-1-[2-ethylthio-2-methylpropylamino]-benzene 2-(2-mercapto-2-methylpropylamino)-1-[2-ethylthio-2-methylpropylamino]benzene was reacted with Tc-99m sodium pertechnetate by the method of Example 7. The product was purified by filtration through a 0.22 micron Millex GS filter to produce a 1.09 mCi/ml solution of the Tc-99m complex of 2-(2-mercapto-2-methylpropylamino)-1-[2-ethylthio-2-methylpropylamino]benzene.

HPLC (90% ethanol/H$_2$O, 1.5 ml/min, C18 Radial Pak) Rt 3.76 min, radiochemical purity 100%. TLC (50% diethyl ether/chloroform) Rf 0.71, radiochemical purity 98%. Electrophoresis (0.05M NaH$_2$PO$_4$, pH 4.5, 300 volts, 45 min Whatman 3MM paper) neutral. Partition coefficient (octanol/H$_2$O NaH$_2$PO$_4$ pH 7.4) 81.

EXAMPLE 35

2-(1-Methylethylthio)-2-methylpropanalethylenedioxy acetal

2-Mercapto-2-methylpropanalethylenedioxy acetal (1.62 g, 1.09×10$^{-2}$ mol, 100 M%) and 2-iodopropane (2.05 g, 1.20×10$^{-2}$ mol, 110 M%) were treated with sodium hydride (0.29, 1.20×10$^{-2}$ mol, 110 M%) in tetrahydrofuran (50 ml) for 24 hr as described in Example 20. Extraction and solvent removal as described in Example 20 provided 1.46 g (70% yield) of 2-(1-methylethylthio)-2-methylpropanalethylenedioxy acetal as a light yellow liquid.

EXAMPLE 36

2-(1-Methylethylthio)-2-methylpropanal 2-(1-Methylethylthio)-2-methylpropanalethylenedioxy acetal (1.46 g, 7.68×10$^{-3}$ mol) was heated for 2 hr in 0.5M HCl (25 ml) and tetrahydrofuran (25 ml) and isolated as described in Example 21 to give 2-(1-methylethylthio)-2-methylpropanal 1.35 g (100%) of a light yellow liquid containing traces of tetrahydrofuran.

EXAMPLE 37

2-(2-Mercapto-2-methylpropylamino)-1-[2-(1-methylethylthio)-2-methylpropylamino]benzene 2-Amino-1-(2-mercapto-2-methylpropylamino)benzene (0.515 g, 2.65×10$^{-3}$ mol) and 0.786 g (5.31×10$^{-3}$ mol, 200 M%) 2-(1-methylethylthio)-2-methylethylthio)-2-methypropanal were reacted by the method of Example 2 to give 2-(2-mercapto-2-methylpropylamino)-1-[2-(1-methylethylthio)-2-methylpropylamino]benzene 0.244 g (28% yield) as a colorless oil after purification by radial chromatography on a 2 mm silica gel plate eluting with 100 ml 100% petroleum ether and 200 ml 5% diethyl ether/petroleum ether.

EXAMPLE 38

Tc-99m complex of 2-(2-Mercapto-2-methylpropylamino)-1-[2-(1-methylethylthio)-2-methylpropylamino]benzene 2-(2-Mercapto-2-methylpropylamino)-1-[2-(1-methylethylthio)-2-methylpropylamino] benzene was reacted with sodium pertechnetate Tc-99m according to the method of Example 7 to produce the Tc-99m complex of 2-(2-mercapto-2-methylpropylamino)-1-[2-(1-methylethylthio)- 2-methylpropylamino] benzene. The product was purified by injecting the crude mixture into the HPLC and collecting fractions.

EXAMPLE 39

1-[2-Methylthio-2-methylpropylamino]-2-(2-mercapto-2-methylpropylamino)benzene 1,2-Bis (2-Mercapto-2-methylpropylamino)benzene (0.47 g, 1.69×10$^{-3}$ mol), and 0.09 g (1.85×10$^{-3}$ mol, 110 M%) sodium hydride were dissolved in 25 ml tetrahydrofuran. Methyl iodide (0.080 ml, 1.27×10$^{-3}$ mol, 75 M%) was added, and the mixture was stirred under nitrogen for 1 hour. The excess hydride was destroyed by the slow addition of 10 ml 0.5M HCl. The mixture was shaken with a mixture of 100 ml ether and 100 ml 0.5 N HCl. The aqueous layer was extracted with an additional 50 ml portion of ether, and the combined ether layers were washed with 100 ml saturated NaCl. The ether layer was then dried over anhydrous Na$_2$SO$_4$. Rotary evaporation yielded 0.30 g (94% yield) of 1-[2-methylthio-2-methylpropylamino]-2-(2-mercapto-2-methylpropylamino)benzene as a yellow oil. Isolation was performed by radial chromatograph on a 1 mm silica plate, using petroleum ether: ethyl acetate-80:20 as the eluting solvent to give yielding a mixture of the 1-[2-methylthio-2-methylpropyl- amino]-2-(2-mercapto-2-methylpropylamino)benzene, S,S'-dimethyl, and the dithiol starting material.

EXAMPLE 40

1-[2-(2-Methyl-2-propenylthio)-2-methylpropylamino]-2-(2-mercapto-2-methylpropylamino)benzene 1,2-Bis (2-mercapto-2-methylpropylamino)benzene (0.304 g, $1.07 \times 10^{-3}$ mol) was dissolved in 15 ml tetrahydrofuran. Sodium hydride (0.06 g, $1.25 \times 10^{-3}$ ml, 116 M%) and 0.095 ml ($9.63 \times 10^{-4}$ mol, 90 M%) 3-chloro-2-methylpropene were added. The mixture was stirred at room temperature, under nitrogen, for 1.5 hours. The reaction mixture was worked up as stated in Example 39. Product was isolated by radial chromatography on a 1 mm silica plate using hexane:ethyl acetate-90:10 as the eluting solvent to give 100 mg (27% yield) as a mixture containing 50% of 1-[2-(2-methyl-2-propenylthio)-2-methylpropylamino]-2-(2-mercapto-2-methylpropylamino)benzene 11% of the dithiol and 35% of the disubstituted compound.

EXAMPLE 41

2-(2-Butylthio-2-methylpropylamino]-1-(2-mercapto-2-methylpropylamino)benzene 1,2-Bis (2-mercapto-2-methylpropylamino)benzene (0.17 g, $6.1 \times 10^{-4}$ mol, 120 M%) and 0.07 g ($5.1 \times 10^{-4}$ mol, 100 M%) 1- bromobutane were dissolved in 25 ml tetrahydrofuran (freshly distilled over Na). Sodium hydride (0.03 g, $6.25 \times 10^{-4}$ mol, 102 M%) was then added. The mixture was stirred at room temperature under nitrogen for 3 hours. The reaction mixture was worked up as in Example 40. The product was isolated by radial chromatography on 1 mm silica plate, using hexane: ethyl acetate as the eluting solvent, giving 40 mg (23% yield) 2-(2-butylthio-2-methylpropylamino]-1-(2-mercapto-2-methylpropylamino)benzene as a yellow oil.

EXAMPLE 42

2-(2-Mercapto-2-methylpropylamino)1-[2-(1-methylpropylthio)-2-methylpropylamino)benzene 1,2-Bis (2-mercapto-2-methylpropylamino)benzene (287 mg, 1.01 mmol, 100 M%) was treated with sodium hydride (24 mg, 1.01 mmol, 100 M%) and 2-iodobutane (162 mg, 0.90 mmol, 90 M%) as described in Example 32. The product was purified twice by successive radial chromatography using 3% ether/petroleum ether to elute the product. Concentration of the desired fractions gave 71 mg (21%) of 2-(2-mercapto-2-methylpropylamino)-1-[2-(1-methylpropylthio-2-methylpropylamino)benzene a colorless oil.

EXAMPLE 43

Tc-99m complex of 2-(2-Butylthio)2-methylpropylamino]-1-(2-mercapto-2-methylpropylamino)-benzene 2-(2-(Butylthio)2-methylpropylamino]-1-(2-mercapto-2-methylpropylamino)benzene was reacted with Tc-99m sodium pertechnetate by the method of Example 7 to produce Tc-99m complex of 2-(2-butylthio)2-methylpropylamino)-1-(2-mercapto-2-methylpropylamino)-benzene. The complex was purified by filtration through Millex GS and Jelco 5 micron fitlers. HPLC (90% ethanol/H 2 O, 1.5 ml/min, C18 5 micron Radial Pak) Rt 4.4 min (99%). TLC (50% diethyl ether/-chloroform) Rf 0.89, radiochemical purity 92%. Electrophoresis (0.05 M $NaH_2PO_4$, buffer pH 4.5 constant 300 volts, 30 min) neutral.

EXAMPLE 44

Tc-99m complex of 1-[2-Methylthio-2-methylpropylamino]-2-(2-mercapto-2-methylpropylamino)-benzene 1-[2-Methylthio-2-methylpropylamino]-2-(2-mercapto-2-methylpropylamino)benzene was reacted with Tc-99m sodium pertechnetate by the method of Example 7 to produce the Tc-99m complex of 1-[2-methylthio-2-methylpropylamino]-2-(2-mercapto-2-methylpropylamino)benzene. HPLC (80% ethanol/$H_2O$, 1.5 ml/min, C18 5 micron Nova Pak) Rt 4.34 min (92%). TLC (50% chloroform/diethyl ether) Rf 0.75, radiochemical purity 95%. Electrophoresis (0.05 M $NaH_2PO_4$, pH 4.5, 300 volts, 30 min) neutral.

EXAMPLE 45

Tc-99m complex of 1-[2-(2-Methyl-2-propenylthio)-2-methylpropylamino]-2-(2-mercapto-2-methylpropylamino)benzene 1-[2-(2-Methyl-2-propenylthio)-2-methylpropylamino]-2-(2-mercapto-2-methylpropylamino)benzene was reacted with Tc-99m sodium pertechnetate by the method of Example 7 to produce Tc-99m complex of 1-[2-(2-methyl-2-propenylthio)-2-methylpropylamino]-2-(2-mercapto-2-methylpropylamino)benzene. HPLC (90% ethanol:$H_2O$, 1.5 ml/min, C18 5 micron Nova Pak) Rt 3.65 min (100%). TLC (50% diethyl ether: chloroform (Rf 0.58, radiochemical purity 96%. Electrophoresis (0.05M $NaH_2PO_4$, pH 4.5, 300 volts, 30 min) neutral.

EXAMPLE 46

Tc-99m complex of 2-(2-Mercapto-2-methylpropylamino)-1-[2-(1-methylpropylthio)-2-methylpropylamino)benzene 2-(2-Mercapto-2-methylpropylamino)-1-(2-(1-methylpropylthio)-2-methyl-propylamino)benzene was reacted with sodium pertechnetate Tc-99m according to the method of Example 7 to produce the Tc-99m complex of 2-(2-mercapto-2-methylpropylamino)-1-[2-(1-methylpropylthio)-2-methylpropylamino)benzene. The produce was purified by filtration through a 0.22 micron Millex GS filter. HPLC (90% ethanol/$H_2O$, 1.5 ml/min, Waters Radial-Pak C18) Rt 4.01 min, radiochemical purity 95.5%. TLC (30% ethyl acetate/hexane) Rf 0.33, radiochemical purity 93.2%; (ethyl acetate/methanol/water/15 M $NH_4OH$— 86:10:3:1) Rf 0.83, radiochemical purity 97.5%. Electrophoresis (0.05M $NaH_2PO_4$, pH 4.5, 300 volts, 45 min, Whatman 3MM paper) neutral.

EXAMPLE 47

1-(2-Vinylthio-2-methylpropylamino)-2-(2-mercapto-2-methylpropylamino)benzene 1,2,3,6,7,8-Hexahydro-3,3,6,6-tetramethyl-4,5,1,8-benzodithiadiazacyclodecine (0.34 g, $1.21 \times 10^{-3}$ mol, 100 M%) was placed in a flame dried round bottom under nitrogen. Vinylmagnesium bromide (1.0M in tetrahydrofuran (13.6 ml, $1.36 \times 10^{-2}$ mol, 1124 M%) was added to the solid and the solution was heated at reflux for 1.5 hr. The reaction was quenched with $2 \times 75$ ml ether. The ether layers were combined, washed with 40 ml saturated sodium chloride solution and dried over $Na_2SO_4$. The ether was removed on the rotary evaporator to obtain the crude oily product. The product was purified by radial chromatography on a 2 mm silica plate and eluting with 90% petroleum ether/ethyl acetate to obtain 0.15 g (40%) 1-(2-vinylthio-2-methylpropylamino)-2-(2-mercapto-2-methylpropylamino)-benzene as an oil.

EXAMPLE 48

Tc-99m complex of 1-(2-Vinylthio-2-methylpropylamino)-2-(2-mercapto-2-methylpropylamino)benzene 1-(2-Vinylthio-2-methylpropylamino)-2-(2-mercapto-2-methylpropylamino)benzene was reacted with Tc-99m sodium pertechnetate by the method of Example 7 to produce the Tc-99m complex of 1-(2-vinylthio-2-methylpropylamino)-2-(2-mercapto-2-methylpropylamino)benzene in 68% yield. HPLC (90% ethanol:H$_2$O, 1.5 ml/min, C18 5 micron Nova Pak) 3.46 min (93%). TLC (10% ethyl acetate:petroleum ether) Rf 0.40, radiochemical purity 94%. Electrophoresis (0.05M NaH$_2$PO$_4$ buffer, pH 4.5, 300 volts, 30 min) neutral.

EXAMPLE 49

2-Amino-3-(2-mercapto-2-methylpropylamino)toluene 2,3-Diaminotoluene (1.50 g, 1.22×10$^{-2}$ mol) and 1.08 g (1.23×10$^{-2}$ mol) isobutylene sulfide were placed in a Teflon-lined bomb and heated to 110° C. for 8 hours. After cooling to room temperature, the oily residue was dissolved in 100 ml ethyl acetate and washed with 100 ml water, followed by 100 ml saturated NaCl. The ethyl acetate was then dried over anhydrous Na$_2$SO$_4$ and removed on the rotary evaporator. The residue (2.0 g, 80% yield) was purified on a 500 ml sintered glass funnel silica bed, using 90% hexane:ethyl acetate as the eluting solvent, to give 0.40 g (16% yield) of 2-amino-3-(2-mercapto-2-methylpropylamino)toluene as an oil.

EXAMPLE 50

2-Butylthio-2-methylpropanalethylenedioxy acetal

2-Mercapto-2-methylpropanalethylenedioxy acetal (3 g, 2.0×10$^{-2}$ mol) and 3.03 g (2.2×10$^{-2}$ mol, 110 M%) 1-bromobutane were dissolved in 25 ml tetrahydrofuran (freshly distilled over sodium). The system was purged with nitrogen and 1.16 g (2.4×10$^{-2}$ mol, 120 M%) sodium hydride (washed with 2×10 ml portions of hexane) was added. The solution was stirred at room temperature under nitrogen for 24 hours. Thereafter, the excess hydride was destroyed by the addition of 10 ml methanol. The solution was shaken with a mixture of 100 ml diethyl ether and 100 ml 0.5M NaOH. The ether layer was washed with 100 ml saturated NaCl, then dried over anhydrous Na$_2$SO$_4$. Rotary evaporation yielded 3.73 g (90% yield) of 2-butylthio-2-methylpropanalethylenedioxy acetal as an oil.

EXAMPLE 51

2-Butylthio-2-methylpropanal

2-Butylthio-2-methylpropanalethylenedioxy acetal, (3.73 g, 1.82×10$^{-2}$ mol) was placed in a 100 ml round-bottom flask, then a mixture of 20 ml methanol, 20 ml H$_2$O, and 5 ml 12M HCl was added, and the solution was refluxed for 2 hours. The mixture was extracted with 100 ml diethyl ether and 100 ml water. The ether layer was then dried over Na$_2$SO$_4$. Rotary evaporation yielded 2.4 g (80% yield) of 2-butylthio-2-methylpropanal as a yellow oil.

EXAMPLE 52

2-(2-Butylthio)-2-methylpropylamino)-1-(2-mercapto-2-methylpropylamino)-3-methylbenzene 2-Amino-3-(2-mercapto-2-methylpropylamino)toluene (0.69 g, 3.3×10$^{-3}$ mol) and 0.91 g (5.25×10$^{-3}$ mol, 160 M%) 2-butylthio-2-methylpropanal were dissolved in 50 ml methanol and 0.37 ml (6.6×10$^{-3}$ mol, 200 M%) glacial acetic acid was added, followed by 0.62 g (9.9×10$^{-3}$ mol, 300 M%) sodium cyanoborohydride. The mixture was stirred at room temperature under nitrogen for 20 hr, then 100 ml 0.5M HCl was added and the mixture was extracted with diethyl ether then dried over anhydrous Na$_2$SO$_4$, and removed on the rotary evaporator. The residue (0.80 g, 69% yield) was purified by radial chromatography on a 4 mm silica gel plate, using petroleum ether: ethyl acetate-95% as the eluting solvent, to give 2-(2-butylthio)-2-methylpropylamino)-1-(2-mercapto-2-methylpropylamino-3-methylbenzene, 0.40 g (34% yield) as a yellow oil.

EXAMPLE 53

Tc-99m complex of 2-(2-Butylthio-2-methylpropylamino)-1-(2-mercapto-2-methylpropylamino)-3-methylbenzene 2-[2-(Butylthio)-2-methylpropylamino]-1-(2-mercapto-2-methylpropylamino-3-methylbenzene was reacted with Tc-99m sodium pertechnetate by the method of Example 7 to produce Tc-99m complex of 2-(2-butylthio)-2-methylpropylamino)-1-(2-mercapto-2-methylpropylamino)-3-methylbenzene. The complex was purified by filtration through Millex GS and Jelco 5 micron filters. HPLC (90% ethanol/H$_2$O) 1.5 ml/min, C18 5 micron Radial Pak) Rt 4.74 min (99%). TLC (50% diethyl ether/chloroform) Rf 0.95, radiochemical purity 86%. Electrophoresis (0.05 M NaH$_2$PO$_4$, buffer pH 4.5, 300 volts, 30 min) neutral.

EXAMPLE 54

2-Cyclopropylmethylthio-2-methylpropanalethylenedioxy acetal

2-Mercapto-2-methylpropanalethylenedioxy acetal (3.36 g, 2.27×10$^{-2}$ mol, 100 M%) was dissolved in 100 ml anhydrous tetrahydrofuran. Hexane-washed sodium hydride (1.20 g, 2.50×10$^{-2}$ mol, 110 M%) (50% in oil) was added to the reaction mixture which was stirred at 21° C. for 1.5 hr and then quenched with 100 ml H$_2$O. The reaction solution was extracted with 2×60 ml diethyl ether. The ether layers were combined, washed with 40 ml saturated NaCl solution and then dried (Na$_2$SO$_4$). The solvent was removed on the rotary evaporator to afford 4.03 g (88% yield) of 2-cyclopropylmethylthio-2-methylpropanal-ethylenedioxy acetal as an oil.

EXAMPLE 55

2-Cyclopropylmethylthio-2-methylpropanal

2-Cyclopropylmethylthio-2-methylpropanalethylenedioxy acetal, (3.77 g, 1.87×10$^{-2}$ mol, 100 M%) was placed in a mixture of 15 ml tetrahydrofuran and 40 ml 0.5 M HCl and heated at reflux for 2 hr, then quenched with 40 ml H$_2$O. The reaction was extracted with 2×60 ml diethyl ether, washed with 40 ml saturated NaCl solution, and dried over Na$_2$SO$_4$. The solvent was removed on the rotary evaporator to afford 2.88 g (98% yield) of 2-cyclopropylmethylthio-2-methylpropanal as an oil.

EXAMPLE 56

1-(2-Cyclopropylmethylthio-2-methylpropylamino)-2-(2-mercapto-2-methylpropylamino)benzene.

2-Amino-1-(2-mercapto-2-methylpropylamino)benzene (0.43 g, 2.19×10$^{-3}$ mol) and 0.82 g (5.19×10$^{-3}$ mol, 237 M%) 2-cyclopropylmethylthio-2-methylpropanal were reacted by the method of Example 2 to yield 0.63 g (85%) of 1-(2-cyclopropylmethylthio-2-methylpropylamino)-2-(2-mercapto-2-methylpropylamino)benzene as an oil product after purification by filtration through flash silica in a 350 ml sintered glass funnel, eluting with 200 ml portions of 2×100% hexane, 3×90% hexane/ether, 2×80% hexane/ether.

EXAMPLE 57

Tc-99m complex of 1(2-Cyclopropylmethylthio-2-methylpropylamino)-2-(2-mercapto-2-methyl-propylamino) benzene.

1-[2-Cyclopropylmethylthio-2-methylpropylamino)-2-(2-mercapto-2-methylpropylamino) benzene was reacted with Tc-99m sodium pertechnetate by the method of Example 7 to produce Tc-99m complex of 1-[2-cyclopropylmethylthio-2-methylpropylamino)-2-(2-mercapto-2-methyl-propylamino) benzene. The complex was purified by filtration through a 0.22 micron Millex GS filter. HPLC (80% ethanol/H$_2$O, 1.5 ml/min, Waters Radial-Pak C18) Rt 4.99 min, radiochemical purity 100%. TLC (70% hexane/ethyl acetate) Rf 0.42, radiochemical purity 98%. Electrophoresis (0.05M NaH$_2$PO$_4$, pH 4.5, 300 volts, 45 min) neutral.

EXAMPLE 58

Preparation of a Technetium Kit

In a 10 ml crimp vial, 3.6 mg (1×10$^{-5}$ moles) of the ligand of formula I each as the compound as prepared in Example 26 was dissolved in 5 drops ethanol. The ethanol was then removed with a nitrogen stream, to leave a thin film of solid. Argon purged sterile H$_2$O (9.5 ml) and 0.40 g 2-hydroxypropyl-beta-cyclodextrin (HPCD) were then added. The mixture was sonicated for 10 minutes, and stirred on the vortex mixer for an additional 10 minutes. The mixture was repurged with argon, sealed and crimpled. Stannous chloride (0.60 ml 1 mM) as then added. The 1 MM stannous chloride solution was prepared by the addition of 9.5 mg anhydrous SnCl$_2$ in 50 ml argon-purged water. The mixture was then filtered under argon through a Millex GS filter into six vented 10 ml vials. Approximately 1 ml was dispensed into each vial. The vials were then placed in a vacuum dessicator overnight at 0.5 Torr to give a white solid. Thereafter, the vials were flushed with argon, sealed and crimped. The vials were stored at room temperature protected from light.

EXAMPLE 59

Tc-99m Labeling of the Kit

A kit vial prepared in Example 58 was reconstituted in 1 ml sterile, purged H$_2$O. The mixture was sonicated for 5 minutes, to give a clear solution. Tc-99m NaTcO$_4$ (1 ml 10 mCi/ml) was then added to each vial. Radiolabeling yields were determined by TLC using ethyl acetate/petroleum ether (20:80) as the eluting solvent.

EXAMPLE 60

Biological Evaluation of Tc-99m Complexes

Distribution of the Tc-99m labeled compounds was evaluated in rats. Female Sprague-Dawley rats weighing 140 to 220 g (average 170 g) were anesthetized with sodium pentobarbital and were injected in a tail vein with from 0.05 to 10 mCi of the Tc-99m labeled complex in a volume of 0.2 to 0.5 ml. At least two rats were injected for each time point.

The animals were sacrificed at 5 and 30 minutes after injection and selected organs were removed; the tails were discharged to avoid interference from the injection site. The radioactivity in each organ was measured at a standard geometry with a thallium iodide-activated sodium iodide scintillation detector adjusted for the 140 KeV emission of Tc-99m. The organs were also weighed to one hundredth of a gram and the activity was calculated as a percent of administered dose per gram. The results are reported in the following table.

TABLE 1

| | Biological Distribution of Tc-99m Complexes in Rats (Pentobarbital Anesthesia) | | | | | | | | | |
|---|---|---|---|---|---|---|---|---|---|---|
| | % Injected Dose/Gram Tissue (average of 2 rats) Patent | | | | | | | | | |
| | 5 min | | | | | 30 min | | | | |
| Example # | Blood | Brain | Heart | Brain: Blood | Heart: Blood | Blood | Brain | Heart | Brain: Blood | Heart: Blood |
| 11 | 0.26 | 0.50 | 2.40 | 1.94 | 9.29 | 0.19 | 0.49 | 1.13 | 2.58 | 6.01 |
| 57 | 0.20 | 0.54 | 2.12 | 2.63 | 10.34 | 0.11 | 0.47 | 0.86 | 4.18 | 7.68 |
| 27 | 0.47 | 0.82 | 5.26 | 1.75 | 11.28 | 0.19 | 0.67 | 3.28 | 3.54 | 17.34 |
| 7 | 0.20 | 0.44 | 2.64 | 2.17 | 13.00 | 0.12 | 0.48 | 1.33 | 4.11 | 11.36 |
| 23 | 0.35 | 0.75 | 2.43 | 2.11 | 6.86 | 0.23 | 0.69 | 1.01 | 3.06 | 4.44 |
| 38 | 0.34 | 0.73 | 2.48 | 2.13 | 7.22 | 0.27 | 0.67 | 1.04 | 2.44 | 3.78 |
| 46 | 0.23 | 0.64 | 2.96 | 2.81 | 12.94 | 0.15 | 0.57 | 1.28 | 3.71 | 8.35 |
| 34 | 0.14 | 0.88 | 2.47 | 6.26 | 17.48 | 0.11 | 0.71 | 1.02 | 6.21 | 8.94 |
| 53 | 0.76 | 0.29 | 1.58 | 0.38 | 2.06 | 0.41 | 0.29 | 0.85 | 0.71 | 2.09 |
| 43 | 0.81 | 0.41 | 2.02 | 0.51 | 2.50 | 0.35 | 0.43 | 0.96 | 1.24 | 2.77 |
| 44 | 0.12 | 0.78 | 1.48 | 6.46 | 12.16 | 0.07 | 0.44 | 0.50 | 6.19 | 7.12 |
| 45 | 0.30 | 0.60 | 3.40 | 2.01 | 11.40 | 0.19 | 0.55 | 2.24 | 2.90 | 11.81 |
| 48 | 0.61 | 0.56 | 3.51 | 0.92 | 5.75 | 0.30 | 0.57 | 3.05 | 1.92 | 10.32 |
| 19 | 0.36 | 0.80 | 3.40 | 2.20 | 0.32 | 0.18 | 0.69 | 1.52 | 3.76 | 8.30 |
| 15 | 0.27 | 0.99 | 4.37 | 3.61 | 15.97 | 0.13 | 0.75 | 2.25 | 5.63 | 16.77 |

EXAMPLE 61

2-Acetylthio-2-methylpropanoic acid

Three 100 g bottles of 2-bromo-2-methylpropanoic acid with the lids loosened slightly were placed in a boiling water bath. The molten contents of the bottles were poured into a tared 250 ml erlenmeyer to obtain 302.35 g (1.810 mol, 100 M%) of the acid.

Dimethylformamide (DMF), 100 ml was poured into a 4 l indented 3 neck round bottom flask equipped with a nitrogen bubbler and an overhead stirrer (glass shaft, teflon paddle). The hot 2-bromo-2-methylpropionic acid was then added to the flask through a powder funnel. The flask and the funnel were rinsed with 4×100 ml portions of DMF and were added to the reaction flask. A thermometer was placed in the third neck and the stirred solution was cooled under an atmosphere of nitrogen to −45° C. by placing it in a methanol/water 50:50 dry ice bath. The thermometer was removed and potassium carbonate 250.21 g (1.810 mol, 100 M%) was added through a powder funnel over a 5 minute period. The reaction mixture warmed to −40° C. but there was no apparent reaction and the carbonate did not dissolve. The soluton was diluted with 200 ml DMF and potassium thioacetate 407.10 g (3.564 mol, 196.9 M%) was added through a powder funnel over a 5 minute period. The powder funnel was rinsed with 300 ml DMF which was added to the reaction solution which had warmed to −30° C. The reaction was alowed to slowly warm up as the dry ice was consumed. When the reaction temperature reached −10° C. the reaction began to bubble. The reaction was allowed to warm slowly to room temperature and was stirred under nitrogen for 22 hours. Water, 2 l, and 500 ml concentrated hydrochloric acid were mixed and cooled to 9° C. in an ice bath. The tan colored reaction mixture was slowly poured into the stirred acid solution over a 25 minute period. The reaction flask was washed with 2×100 ml portions of deionized water which was added to the acid solution (10° C., pH 1.5). The acid solution was poured into a 4 l separatory funnel and was extracted sequentially with 3×500 ml and 1×250 ml ethyl acetate. Each organic extract was washed with a separate 100 ml portion of saturated sodium chloride solution. The organic extracts were combined and dried over 400 g of anhydrous sodium sulfate. The solution was filtered through a fluted filter paper into a 2,000 ml round bottom flask and the solvent was removed in two portions under reduced pressure on the rotary evaporator. The sodium sulfate was washed with 3×100 ml portions of ethyl acetate which were filtered into the 2,000 ml round bottom. After all the solvent was removed, the rotary evaporator was connected to the high-vacuum pump and the water bath was heated to 100° C. The product was removed after 1.5 hour to afford 241.07 g of the crude brown oily product which crystallized on cooling. The crystalline mass was placed under high vacuum at 22° C. for 16 hours to afford 240.51 g (82% yield) of the crude crystalline 2-acetylthio-2-methylpropanoic acid.

EXAMPLE 62

2-Mercapto-2-methylpropanoic acid

2-Acetylthio-2-methylpropanoic acid 230.41 g (1.422 mol, 100 M%) was placed in a 2 l round bottom flask, equipped with a magnetic stir bar. The crude solid material was dissolved in 250 ml methanol while stirring.

Methanol, 900 ml, was poured into a 3-l three-neck flask equipped with a magnetic stir bar and a reflux condenser with a nitrogen bubbler on top. The other two necks were stoppered until the flask was flushed with nitrogen. One of the stoppers was removed and, hexane washed sodium spheres (73.16 g, 3.18 mol, 224 M%) were added through a powder funnel over a 20 minute period. The methanol solution bubbled vigorously and was heated to reflux by the chemical reaction.

Both methanol solutions were chilled in an ice bath after all of the sodium had dissolved. The sodium methoxide solution was then poured, all at once, into the chilled solution of 2-acetlythio-2-methylpropanoic acid which warmed to 38° C. The reaction solution was cooled to 20° C. then the ice bath was removed and the solution was stirred at room temperature for 25 minutes. The reaction solution was then chilled in an ice bath to 10° C. over 20 minutes and poured into a 6 l erlenmeyer flask containing a solution of 300 ml concentrated HCl and 700 ml deionized water at 10° C. This solution was extracted with 1×1 l and 2×500 ml portions of ethyl acetate. The ethyl acetate extracted was washed with the same two 300 and 200 ml portion of saturated sodium chloride solution. The organic layers were combined and the solvent was removed on the rotary evaporator to afford an oil which was dissolved in 250 ml ethyl acetate. The ethyl acetate solution was washed with 150 ml saturated sodium chloride solution and then the organic layer was dried over 208 g anhydrous sodium sulfate. The ethyl acetate solution was filtered through a fluted filter paper into a 2 l round bottom flask. The solvent was removed under reduced pressure on the rotary evaporator. The rotary evaporator was connected to the vacuum pump for 15 minutes (0.10 mmHg 51° C. water bath) to afford 160.661 g of 2-mercapto-2-methylpropanoic acid as a brown oil (94% yield) which crystallized when cooled in the refrigerator.

EXAMPLE 63

2-Methyl-2-(2-propynylthio)propanoic acid

Potassium carbonate, 346.26 g (2.505 mol, 220 M%) was dissolved in 1,750 ml deionized water in a 4 l indented round bottom flask equipped with a magnetic stir bar. The carbonate solution was cooled in an ice bath to 6° C.

The 2-mercapto-2-methylpropanoic acid was dissolved in a solution containing 1 l methanol and 186.67 g (2.505 mol, 200 M%) propargyl chloride. This solution was then added to the cold carbonate solution. The round bottom that had contained the acid was washed with 2×100 ml portions of methanol added to the reaction solution which was 15° C. The reaction was removed from the ice bath 30 minutes after the initial mixing and stirred at room temperature (22° C.) for 3.5 hours. The reaction was quenched by pouring it slowly into a chilled solution containing 350 ml concentrated hydrochloric acid and 1500 ml deionized water. The acid solution was extracted with 3×400 ml portions of ethyl acetate. The organic layers were combined and washed with 2×300 ml portions of saturated sodium chloride solution, then dried over 212 g anhydrous sodium sulfate. The dried organic solution was filtered through a sodium sulfate. The dried organic solution was filtered through a fluted filter paper. The solvent was removed under reduced pressure on the rotary evaporator. The crude oily product was then subjected to high-vacuum (0.09 mmHg) for 30 minutes at 40° C. to obtain 172.13 g of crude brown oil (86.97% yield) which crystallized when chilled. Ethyl acetate, 210 ml, was added to the crude crystalline product which had been stored 2 days in the refrigerator. White solid remained after all of the crude product went into solution. The solution was then filtered under vacuum through a 60 ml sintered glass funnel ½ full of Celite. The round bottom and the filter were washed with 3×50 ml portions of ethyl acetate. The filtrates were combined and the solvent was removed to afford 170.20 g of crude oily product in a 500 ml round bottom flask. The round bottom was then equipped with 16.5 cm 14/20 Vigreaux distillation column topped with a short path still head and a 3 necked cow. The product was distilled at 0.2 mmHg, 104°–109° C. to collect 118.69 g (fraction #2) of purified 2-methyl-2-(2-propynylthio)-propanoic acid product (60% yield) which crystallized on standing.

EXAMPLE 64

2-Amino-2-(2-mercapto-2-methylpropylamino)benzene

In a 200 ml pressure bottle, 30 g (0.34 mol, 100 ml %) isobutylene sulfide and 51 g (0.47 mol, 140 mol %) o-phenylenediamine (Synder et al. *J. Am. Chem. Soc.* 69:2672–2674, 1947) were dissolved in 20 ml ethanol. The mixture was placed in a 100° C. oil bath, with stirring, for 5 hours. The vessel was allowed to cool to room temperature, and the crude mixture was transferred to a 500 ml round bottom flask. The ethanol was removed on a rotary evaporator to give 77 g of a heterogeneous brown oil. The crude product was diluted with 200 ml diethyl ether and washed with 3×200 ml 0.5 N NaOH. The combined base layers were then acidified to pH 1 by the slow addition of 40 ml concentrated HCl. The acid layer was extracted with 3×200 ml diethyl ether. The pH of the aqueous layer was then adjusted to pH 4 by the addition of 9 g sodium hydroxide pellets, and extracted with 3×200 ml diethyl ether. The combined ether layers from the pH 4 extract were washed with 100 ml saturated NaCl and dried over 18 g anhydrous sodium sulfate. The solvent was then removed on a rotary evaporator to give 2.6 g (40% yield) of 2-amino-1-(2-mercapto-2-methylpropylamino)benzene as a gold oil which solidified.

EXAMPLE 65

2-(2-Mercapto-2-methylpropylamino)-1-(2-methylpropylamido)benzene

In a 500 ml round bottom flask equipped with a $N_2$ inlet and a reflux condensor, 22 g (0.14 mol, 100 ml %) 2-methyl-2-(2-propynylthio)propanoic acid was dissolved in 100 ml toluene. Thionyl chloride (15.3 ml, 0.21 mol, 150 mol %) was added in one portion. The mixture was heated at reflux for 1 hour. Gas evolution was noted during this time. The excess thionyl chloride was then removed by distillation. In a separate 500 ml round bottom flask equipped with a $N_2$ inlet and a 100 ml addition funel, 27 g (0.14 mol, 100 mol %) 2-amino-1-(2-mercapto-2-methylpropylamino)benzene was dissolved in 100 ml tetrahydrofuran. Triethylamine (23 ml 0.16 mol, 120 mol %) was then added, and the mixture was cooled to 5° C. with an ice-H₂O bath. The acid chloride was transferred to the addition funnel and added dropwise to the amine solution over a period of 2 hours. The mixture was stirred under $N_2$ for 18 hours. The solvent was then removed on a rotary evaporator, and the resulting residual brown oil was diluted with 300 ml ethyl acetate. The ethyl acetate was washed sequentially with 100 ml 0.5ml M NaOH and 100 ml 0.5M HCl. The acid and base layers were both extracted with an additional 300 ml ethyl acetate. The combined organic layers were then washed with 100 ml saturated NaCl an drived over 50 g anhydrous sodium sulfate. The sodium sulfate was washed with an additional 100 ml ethyl acetate. The solvent was removed on the rotary evaporator to give 52 g (110% yield) of a brown oil which solidified upon standing. The crude solid was adsorbed onto 25 g of silica which was then placed on a 200–270 g bed of silica and eluted with 2000 ml 20% ethyl acetate/hexane. The appropriate fractions were combined and concentrated on the rotary evaporator to give 42 g (89% yield) of an orange oil which solidified. This solid was recrystalized from ethyl acetate and hexane and decolorized with 3 g activated charcoal. The solution was allowed to sit at room temperature for 5 hours, then stored at 0° C. for 18 hours. The resulting beige amorphous solid was collected on a sintered glass funnel and rinsed with 200 ml hexane. The crystals were placed in a drying dish and placed in a vacuum desiccator (0.40 Torr) for 18 hours. A total of 21.5 g (46% yield) of 2-(2-mercapto-2-methylpropylamino)-1-[2-(2-propynylthio-2-methylpropylamido) benzene was obtained.

EXAMPLE 66

2-(2-mercapto-2-methylpropylamino)-1-(2-propynylthio)-2-methylpropylamino]benzene In a 2000 ml three-neck round bottom flask equipped with a thermometer, a $N_2$ inlet, and an overhead stirrer, 21.41 g (0.064 mol, 100 mol %) 2-(2-mercapto-2-methylpropylamino)-1-[2-propynylthio)-2-methylpropylamide)benzene was dissolved in 1000 ml anhydrous diethyl ether. The mixture was cooled to −25° C. with a $CCl_4$-$CO_2$ bath. Lithium aluminum hydride (14.50 g, 0.38 mol, 600 mol %) was added in three 4.8 g portions over a period of 30 minutes. The mixture became viscous and white soon after addition, and then turned green. The mixture was stirred under $N_2$ for 14 hours, and then an additional 4.84 g (0.127 mol, 200 mol %) LiAlH₄ and 250 ml diethyl ether were added. The mixture was allowed to stir for an additional 18 hours, then placed in a −20° C. ethylene glycol cooling bath without stirring, for 48 hours. The reaction flask was then placed in a methanol-ice bath and maintained at −10° C. with the periodic addition of ice. In a 250 ml erlenmyer flask, 27.50 g (0.51 mol) ammonium chloride was dissolved in 100 ml deionized H₂O. The aqueous ammonium chloride solution was then added dropwise to the reaction mixture with stirring over a period of 20 minutes. No gas emission was noted after this time, and a white precipitate formed. Hydrochloric acid (500 ml, 0.5M) and 500 ml, 1.5M) were added to dissolve the solids. The mixture was transferred to a 4000 ml separatory funnel, and extracted with 3×200 ml diethyl ether. The combined ether layers were washed with 200 ml saturated NaCl, and dried over 200 g anhydrous sodium sulfate. The sodium sulfate was washed with an additional 100 ml portion of ethyl acetate. The solvent was removed on the rotary evaporator to give 23.7 g (115% yield) of a gold oil. The crude oil was absorbed onto a 20 g silica, and placed on 200–270 g bed of silica. The column was washed with 2000 ml 5% ethyl acetate/hexane. The appropriate fractions were combined, and concentrated on a rotary evaporator to give two fractions of 2-(2-mercapto-2-methylpropylamino)-1-[2-(2-propynylthio)-2-methylpropylamino]-benzene as product; 7.75 g (38% yield, 91% purity), and 9.25 g (45% yield, 95% purity).

EXAMPLE 67

2-(2-mercapto-2-methylpropylamino)-1-[2-(2-propynyl-thio)-2-methylpropylamino]benzene hydrochloride The HCl salt of each 2-(2-mercapto-2-methyl-propylamino)-1-[2-(2-propynylthio)-2-methylpropyl-amino]benzene fraction was made by separately dissolving the free amine in 100 ml diethyl ether and cooling the mixture in an ice-H$_2$O bath to 5° C. Anhydrous HCl gas was bubbled through the solution for 3 minutes, which resulted in the precipitation of an amorphous beige solid. The HCl gas and diethyl ether were removed by placing the solution in a 40° C. water bath, and passing a nitrogen stream over the solution. The first sample was recrystallized from ethanol and hexane to give 8.5 g (37% yield, 98.5% purity) of a crystalline, white solid. The second fraction required three successive recrystallizations to obtain a similar purity; 6 g (26% yield, 98% purity). A total of 14.5 g (65% yield) of 2-(2-mercapto-2-methylpropylamino)-1-[2-(2-propynylthio)-2-methylpropylamino]benzene hydrochloride was obtained.

We claim:

1. An agent comprising a complex of a radioactive metal with a compound of the formula

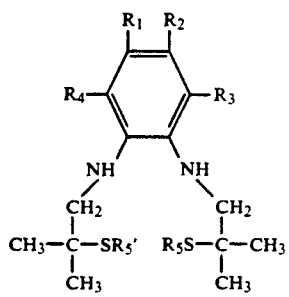

wherein R$_1$, R$_2$, R$_3$, and R$_4$ are halogen, hydrogen or lower alkyl containing from 1 to 7 carbon atoms, with at least one of R$_3$ and R$_4$ being hydrogen; and one of R$_5$ and R$_5'$ being hydrogen whereas the other of said R$_5$ and R$_5'$ being alkyl containing from 1 to 10 carbon atoms, alkenyl containing from 2 to 10 carbon atoms, alkynyl containing from 2 to 10 carbon atoms or lower alkylcycloloweralkyl containing from 4 to 13 carbon atoms; or with a salt thereof.

2. The agent of claim 1 wherein said radioactive metal is technetium 99m.

3. The agent of claim 2 wherein R$_5$ is hydrogen and R$_5'$ is lower alkyl containing from 1 to 7 carbon atoms.

4. The agent of claim 3 wherein R$_5'$ is

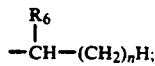

wherein R$_6$ is hydrogen or methyl and n is an integer of from 0 to 5.

5. The agent of claim 4 wherein R$_1$, R$_2$, R$_3$ and R$_4$ are hydrogen.

6. The agent of claim 5 wherein said agent is Tc-99m complex of 2-(2-mercapto-2-methylpropylamino)-1-[2-propylthio-2-methylpropylamino]benzene.

7. The agent of claim 5 wherein said agent is Tc-99m complex of 2-(2-butylthio-2-methylpropylamino)-1-(2-mercapto-2-methylpropylamino)benzene.

8. The agent of claim 5 wherein said agent is Tc-99m complex of 1-[2-methylthio-2-methylpropylamino]-2-(2-mercapto-2-methylpropylamino)benzene.

9. The agent of claim 5 wherein R$_6$ is methyl.

10. The agent of claim 9 wherein said compound is Tc-99m complex of 2-(2-mercapto-2-methyl-propylamino)-1-[2-(1-methylethylthio)-2-methyl-propylamino]-benzene.

11. The agent of claim 9 wherein said compound is Tc-99m complex of 1-(2-mercapto-2-methyl-propylamino)-2-(2-(1-methylpropylthio)-2-methyl-propylamino) benzene.

12. The agent of claim 3 wherein R$_4$ is methyl and R$_1$, R$_2$ and R$_3$ are hydrogen.

13. The agent of claim 12 wherein said compound is Tc-99m complex of 2-(2-butylthio)-2-methyl-propylamino)-1-(2-mercapto-2-methylpropylamino)-benzene.

14. The agent of claim 2 wherein R$_5$ is alkenyl.

15. The agent of claim 14 wherein R$_5'$ is

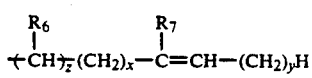

wherein R$_6$ and R$_7$ are individually hydrogen or methyl, x is an integer of from 0 to 3, is an integer from 0 to 2 and z is an integer of from 0 to 1.

16. The agent of claim 14 wherein R$_1$, R$_2$, R$_3$ and R$_4$ are hydrogen.

17. The agent of claim 16 wherein y is an integer from 1 to 2.

18. The agent of claim 17 wherein said compound is Tc-99m complex of 1[2-trans-2-butenylthio)-2-methyl-propylamino]-2-(2-mercapto-2-methylpropylamino) benzene.

19. The agent of claim 14 wherein y is 0.

20. The agent of claim 19 wherein said agent is Tc-99m complex of 2-(2-mercapto-2-methylpropylamino)-1-[2-(4-pentenylthio)-2-methylpropylamino]-benzene.

21. The agent of claim 19 wherein aid compound is Tc-99m complex of 1-[2-(2-methyl-2-propenylthio)-2-methylpropylamino]-2-(2-mercapto-2-methyl-propylamino)benzene.

22. The agent of claim 19 wherein said compound is Tc-99m complex of 1-(2-allylthio-2-methyl-propylamino)-2-(2-mercapto-2-methylpropylamino)-benzene.

23. The agent of claim 19 wherein said compound is Tc-99m complex of 1-[2-(3-butenylthio)-2-methyl-propylamino-2-(2-mercapto-2-methylpropylamino)ben-zene.

24. The agent of claim 19 wherein said compound is Tc-99m complex of 1-(2-vinylthio-2-methyl-propylamino)-2-(2-mercapto-2-methylpropylamino)-benzene.

25. The agent of claim 2 wherein R$_5$ is hydrogen and R$_5'$ is alkynyl.

26. The agent of claim 25 wherein R$_5'$ is

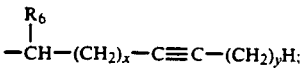

wherein R₆ is hydrogen or methyl, x is an integer from 0 to 3 and y is an integer from 0 to 2.

27. The agent of claim 26 wherein R₁, R₂, R₃ and R₄ are hydrogen.

28. The agent of claim 27 wherein y is 0.

29. The agent of claim 28 wherein said compound is a Tc-99m complex of 2-(2-mercapto-2-methylpropylamino)-1-[2-(2-propynylthio)-2-methylpropylamino]-benzene.

30. The agent of claim 2 wherein R₅' is loweralkylcycloalkyl containing from 4 to 13 carbon atoms.

31. The agent of claim 30 wherein R₅' is

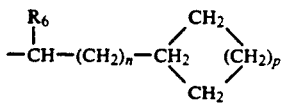

wherein n is an integer of from 0 to 5; p is an integer from 0 to 3 and R₆ is hydrogen or methyl.

32. The agent of claim 31 wherein R₁, R₂, R₃ and R₄ are hydrogen.

33. The agent of claim 32 wherein said compound is Tc-99m complex of 1-(2-cyclopropylmethylthio-2-methylpropylamino)-2-(2-mercapto-2-methylpropylamino)benzene.

34. A method of imaging organs of the body comprising intravenously injecting into a patient an effective amount of a complex of a radioactive metal with a compound of the formula:

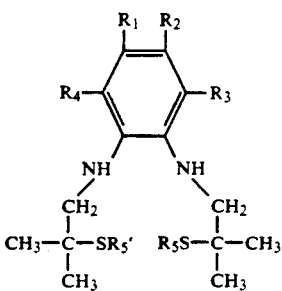

wherein R₁, R₂, R₃ and R₄ are halogen, hydrogen or lower alkyl containing from 1 to 7 carbon atoms with at least one of R₃ and R₄ being hydrogen; and one of R₅ and R₅' being hydrogen whereas the other of said R₅ and R₅' being alkyl containing from 1 to 8 carbon atoms, alkenyl containing from 2 to 10 carbon atoms, alkynyl containing from 2 to 10 carbon atoms or lower alkylcycloloweralkyl containing from 4 to 13 carbon atoms; or with a salt thereof, said complex being injected in a carrier suitable for intravenous injection and scanning the organ to be imaged with scintiscanning means.

35. The method of claim 34 wherein said radioactive metal is technetium 99m.

36. The method of claim 35 wherein the organ to be imaged is the brain.

37. The process of claim 36 wherein R₅' is

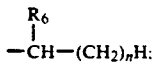

wherein R₆ is hydrogen or methyl and n is an integer of from 0 to 5.

38. The process of claim 36 wherein said complex is Tc-99m complex of 2-(2-mercapto-2-methylpropylamino)-1-(2-propylthio-2-methylpropylamino)-benzene.

39. The process of claim 36 wherein said complex is Tc-99m complex of 2-(2-butylthio-2-methylpropylamino)-1-(2-mercapto-2-methylpropylamino)-3-methylbenzene.

40. The process of claim 36 wherein R₅' is

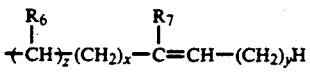

wherein R₆ and R₇ are individually hydrogen or methyl, x is an integer of from 0 to 3, y is an integer from 0 to 2 and z is an integer of from 0 to 1.

41. The process of claim 40 wherein said complex is Tc-99m complex of 2-(2-mercapto-2-methylpropylamino)-1-[2-4-pentenylthio)-2-methylpropylamino]benzene.

42. The process of claim 40 wherein said complex is Tc-99m complex of 1-(2-allylthio-2-methylpropylamino)-2-(2-mercapto-2-methylpropylamino)-benzene.

43. The process of claim 40 wherein said complex is Tc-99m complex of 1-[2-(3-butenylthio)-2-methylpropylamino-2-(2-mercapto-2-methylpropylamino)benzene.

44. The process of claim 36 wherein R₅ is hydrogen and R₅' is alkynyl.

45. The process of claim 44 wherein R₅' is

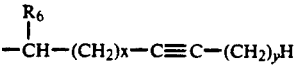

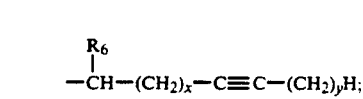

wherein R₆ is hydrogen or methyl, x is an integer from 0 to 3 and y is an integer from 0 to 2.

46. The process of claim 45 wherein said compound is Tc-99m complex of 2-(2-mercapto-2-methylpropylamino)1-[2-(2-propynylthio)-2-methylpropylamino]benzene.

47. The process of claim 36 wherein R₅' is loweralkylcycloalkyl containing from 4 to 13 carbon atoms.

48. The process of claim 47 wherein R₅' is

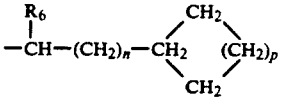

wherein n is an integer of from 0 to 5; p is an integer from 0 to 3 and R₆ is hydrogen or methyl.

49. The process of claim 47 wherein said compound is Tc-99m complex of 1-(2-cyclopropylmethylthio-2-methylpropylamino)-2-(2-mercapto-2-methylpropylamino)-benzene.

* * * * *